US011735206B2

(12) United States Patent
Verbeke et al.

(10) Patent No.: US 11,735,206 B2
(45) Date of Patent: Aug. 22, 2023

(54) EMOTIONALLY RESPONSIVE VIRTUAL PERSONAL ASSISTANT

(71) Applicant: HARMAN INTERNATIONAL INDUSTRIES, INCORPORATED, Stamford, CT (US)

(72) Inventors: Joseph Verbeke, San Francisco, CA (US); Sven Kratz, Saratoga, CA (US); Stefan Marti, Oakland, CA (US)

(73) Assignee: Harman International Industries, Incorporated, Stamford, CT (US)

( * ) Notice: Subject to any disclaimer, the term of this patent is extended or adjusted under 35 U.S.C. 154(b) by 244 days.

(21) Appl. No.: 16/833,203

(22) Filed: Mar. 27, 2020

(65) Prior Publication Data

US 2021/0304787 A1 Sep. 30, 2021

(51) Int. Cl.
*G10L 25/63* (2013.01)
*G06V 40/16* (2022.01)
*B60W 40/08* (2012.01)

(52) U.S. Cl.
CPC ............ *G10L 25/63* (2013.01); *G06V 40/176* (2022.01); *B60W 2040/089* (2013.01)

(58) Field of Classification Search
CPC ....... G10L 25/63; G10L 13/033; G10L 15/22; B60W 40/08; B60W 2040/089; B60W 50/08; B60W 2050/0002; B60W 2050/0057; G06V 40/176; G06V 20/597; G06V 40/174; G06V 40/20; A61B 5/18; A61B 5/6893; A61B 5/165; G06F 3/011; G06F 3/167; G06F 40/216; G06F 40/35; G06F 2203/011; G06F 2203/0381; G06F 40/30; G06F 40/56
See application file for complete search history.

(56) References Cited

U.S. PATENT DOCUMENTS 9,786,299 B2 \* 10/2017 Un ........................ G10L 13/08
10,137,902 B2 \* 11/2018 Juneja .................. B60W 40/09
(Continued)

FOREIGN PATENT DOCUMENTS

WO 2016/089929 A1 6/2016

OTHER PUBLICATIONS

Seo et al., "Automatic Emotion-Based Music Classification for Supporting Intelligent IoT Applications", Electronics, doi:10.3390/electronics8020164, vol. 8, Feb. 2019, pp. 1-20.

*Primary Examiner* — Fariba Sirjani
(74) *Attorney, Agent, or Firm* — I Artegis Law Group, LLP

(57) ABSTRACT

A virtual private assistant (VPA) is configured to analyze various types of input that indicate one or more behaviors associated with a user and to determine the emotional state of the user based on the input. The VPA also determines one or more operations to perform on behalf of the user based on the input and the determined emotional state. The VPA then executes the one or more operations and synthesizes an output based on the emotional state of the user and the one or more operations. The synthesized output includes one or more semantic components and one or more emotional components derived from the emotional state of the user. The VPA observes the behavior of the user in response to the synthesized output and then implements various modifications, based on the observed behavior, to improve the effectiveness of future interactions with the user.

18 Claims, 12 Drawing Sheets

(56) References Cited

U.S. PATENT DOCUMENTS

| | | | |
|---|---|---|---|
| 10,157,626 B2 | 12/2018 | Nahman et al. | |
| 10,399,575 B2 * | 9/2019 | Spasojevic et al. | |
| 10,522,143 B2 * | 12/2019 | Chandrasekaran | G09B 5/00 |
| 10,554,590 B2 * | 2/2020 | Cabrera-Cordon | G06N 5/022 |
| 10,817,316 B1 * | 10/2020 | Young | G06F 16/24575 |
| 10,850,746 B2 | 12/2020 | Marti et al. | |
| 11,186,290 B2 * | 11/2021 | Ito | B60W 40/08 |
| 11,322,143 B2 * | 5/2022 | Horling | G10L 15/30 |
| 11,404,170 B2 * | 8/2022 | Charlap | G16H 80/00 |
| 11,423,895 B2 * | 8/2022 | Hwang | G06N 3/006 |
| 2007/0294229 A1 * | 12/2007 | Au | G06F 16/951 |
| 2008/0096533 A1 * | 4/2008 | Manfredi | G06N 3/006 |
| | | | 455/412.1 |
| 2011/0283190 A1 | 11/2011 | Poltorak | |
| 2016/0163332 A1 * | 6/2016 | Un | G10L 13/033 |
| | | | 704/260 |
| 2016/0236690 A1 * | 8/2016 | Juneja | B60W 50/14 |
| 2017/0124474 A1 * | 5/2017 | Kashyap | G06N 20/00 |
| 2017/0160813 A1 * | 6/2017 | Divakaran | G06N 3/006 |
| 2018/0090137 A1 * | 3/2018 | Horling | G06F 16/9535 |
| 2018/0314689 A1 * | 11/2018 | Wang | G10L 15/1822 |
| 2019/0049957 A1 * | 2/2019 | Healey | A61B 5/0077 |
| 2019/0213264 A1 * | 7/2019 | Antipa | G09F 27/005 |
| 2019/0266999 A1 * | 8/2019 | Chandrasekaran | G10L 15/16 |
| 2019/0325895 A1 | 10/2019 | Bromand et al. | |
| 2019/0355351 A1 * | 11/2019 | Kim | B60W 50/087 |
| 2020/0009739 A1 * | 1/2020 | Moon | G06N 3/0454 |
| 2020/0073885 A1 * | 3/2020 | Baijal | G06F 16/738 |
| 2020/0081535 A1 | 3/2020 | Woo et al. | |
| 2020/0279553 A1 * | 9/2020 | McDuff | G06V 40/174 |
| 2020/0302927 A1 * | 9/2020 | Andruszkiewicz | G06F 40/44 |
| 2021/0064827 A1 * | 3/2021 | Galitsky | G06F 40/284 |
| 2021/0074261 A1 * | 3/2021 | Yang | G10L 13/027 |
| 2021/0304787 A1 * | 9/2021 | Verbeke | B60W 40/08 |

\* cited by examiner

EMOTIONALLY RESPONSIVE VIRTUAL PERSONAL ASSISTANT

BACKGROUND

Field of the Various Embodiments

The various embodiments relate generally to computer software and virtual personal assistants, and more specifically, to an emotionally responsive virtual personal assistant.

Description of the Related Art

A "virtual personal assistant" (VPA) is a type of computer program that interacts with a user to perform various operations on behalf of the user. In so doing, a VPA typically processes vocalizations received from the user and interprets those vocalizations as one or more commands. The VPA then maps those commands to one or more corresponding operations that can be executed on behalf of the user. Upon executing the operations, the VPA can engage with the user conversationally, via a synthesized vocalization, to report the results of the operation. For example, a VPA could process a vocalization received from a user and interpret that vocalization as the command, "check email." The VPA could map that command to an operation for retrieving new emails and execute the operation to obtain new emails for the user. The VPA could then synthesize a vocalization indicating the number of new emails retrieved.

In some implementations, a VPA can be implemented within a vehicle to allow a user to interact with various features of the vehicle without diverting significant attention away from driving. For example, suppose the user needs to adjust the climate control settings of the vehicle to lower the interior temperature to a more comfortable level. The user could vocalize the command "activate air conditioner" in order to instruct the VPA to activate the air conditioner. Upon activating the air conditioner, the VPA could synthesize a vocalization that indicates to the user that the relevant operation has been executed. In this manner, VPAs implemented in vehicles can help users avoid having to divert attention away from driving to manually interact with various vehicle features, thereby increasing overall driving safety.

One drawback of the above techniques is that conventional VPAs can only interpret the semantic components of vocalizations and, therefore, cannot correctly interpret vocalizations that communicate information using emotional components. Consequently, a VPA implemented in a vehicle can sometimes fail to properly perform a given operation on behalf of the user and create a situation where the user has to divert attention away from driving in order to manually perform that operation. For example, suppose a user is listening to the radio and a very loud song suddenly begins to play. The user might quickly instruct the VPA, "decrease volume now!" However, the VPA could fail to interpret the urgency associated with this type of user command and decrease the volume by only one level. To rectify this miscommunication, the user would have to divert attention away from driving and manually decrease the volume of the radio to a more appropriate level, which would decrease overall driving safety.

Another drawback of the above techniques is that, because conventional VPAs cannot correctly interpret vocalizations that communicate information using emotional components, VPAs oftentimes cannot converse with users in a realistic manner. Consequently, a VPA implemented in a vehicle can cause the user to disengage with the VPA or turn the VPA off entirely, thereby creating situations where the user has to divert attention away from driving in order to manually interact with various vehicle features. For example, suppose a user is really excited about receiving a promotion at work and instructs the VPA to determine the fastest route home. If the VPA synthesizes dull, monotone vocalizations to recite the relevant navigation instructions, the user could find the interaction with the VPA depressing and end up turning off the VPA in order to preserve his/her level of excitement. Such outcomes decrease overall driving safety.

As the foregoing illustrates, what is needed in the art are more effective ways for VPAs to interact with users when performing operations on behalf of users.

SUMMARY

Various embodiments include a computer-implemented method for interacting with a user while assisting the user, including capturing a first input that indicates one or more behaviors associated with the user, determining a first emotional state of the user based on the first input, generating a first vocalization that incorporates a first emotional component based on the first emotional state, wherein the first vocalization relates to a first operation that is being performed to assist the user, and outputting the first vocalization to the user.

At least one technical advantage of the disclosed techniques relative to the prior art is that the disclosed techniques enable a VPA to more accurately determine one or more operations to perform on behalf of the user based on the emotional state of the user. Accordingly, when implemented within a vehicle, the disclosed VPA helps to prevent the user from diverting attention away from driving in order to interact with vehicle features, thereby increasing overall driving safety.

BRIEF DESCRIPTION OF THE SEVERAL VIEWS OF THE DRAWINGS

So that the manner in which the above recited features of the various embodiments can be understood in detail, a more particular description of the inventive concepts, briefly summarized above, may be had by reference to various embodiments, some of which are illustrated in the appended drawings. It is to be noted, however, that the appended drawings illustrate only typical embodiments of the inventive concepts and are therefore not to be considered limiting of scope in any way, and that there are other equally effective embodiments.

DETAILED DESCRIPTION

Figure 1A:
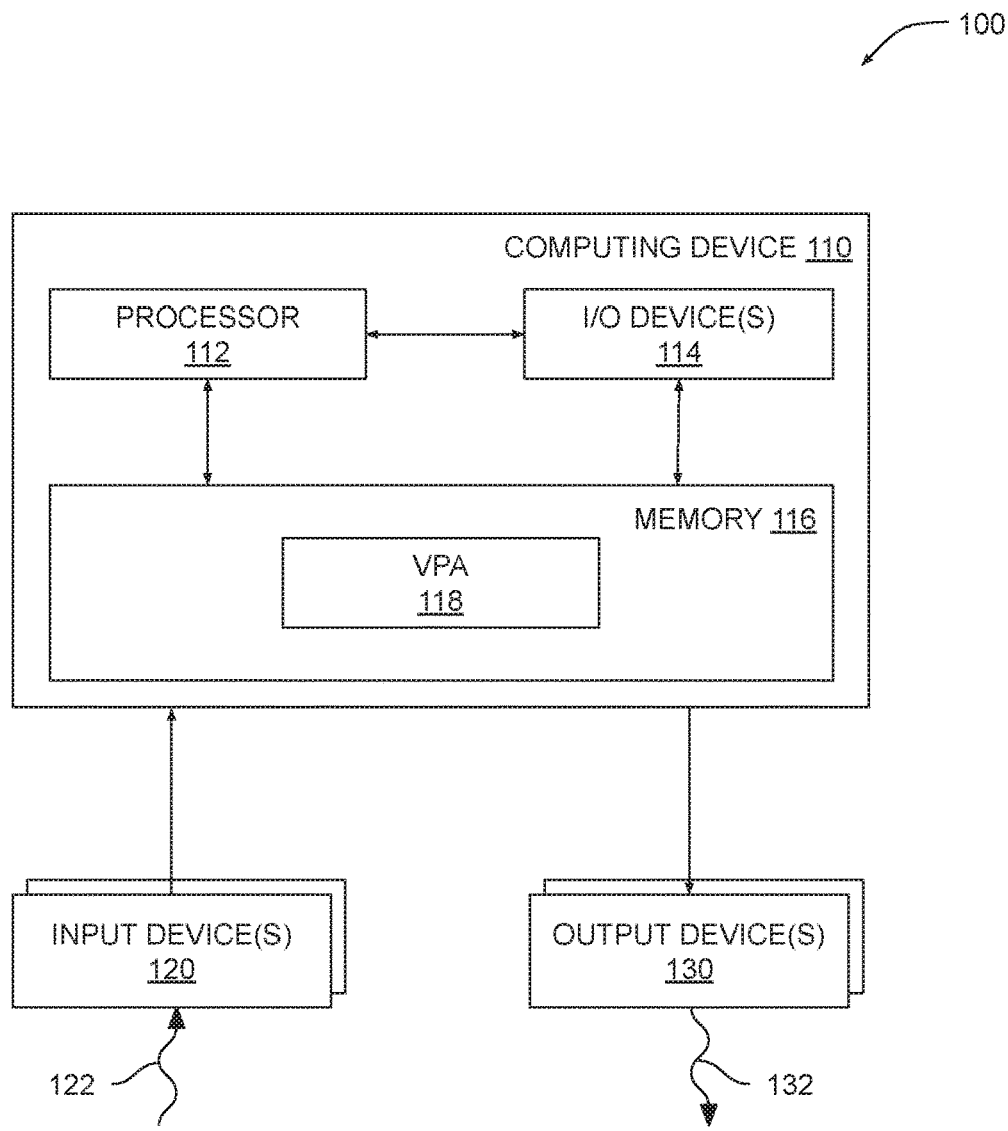
FIGS. 1A-1B illustrate a system configured to implement one or more aspects of the various embodiments.

In the following description, numerous specific details are set forth to provide a more thorough understanding of the various embodiments. However, it will be apparent to one skilled in the art that the inventive concepts may be practiced without one or more of these specific details.

As noted above, conventional VPAs can only interpret the semantic components of vocalizations, and therefore cannot correctly interpret vocalizations that communicate information using emotional components. Consequently, a VPA implemented in a vehicle can sometimes fail to properly perform certain operations on behalf of the user and can therefore create situations where the user has to divert attention away from driving in order to personally perform those operations. In addition, because conventional VPAs cannot correctly interpret vocalizations that communicate information using emotional components, VPAs cannot engage with users conversationally in any sort of realistic manner. Consequently, a VPA implemented within a vehicle can cause the user to disengage with the VPA or turn the VPA off entirely, thereby creating a situation where the user has to divert attention away from driving in order to interact with various vehicle features.

To address these issues, various embodiments include a VPA that is configured to analyze various types of input that indicate one or more behaviors associated with a user. The input may include vocalizations that represent explicit commands for the VPA to execute as well as non-verbal cues associated with the user, such as facial expressions and/or changes in posture, among others. The VPA determines the emotional state of the user based on the input. The VPA also determines one or more operations to perform on behalf of the user based on the input and the determined emotional state. The VPA then executes the one or more operations and synthesizes an output based on the emotional state of the user and the one or more operations. The synthesized output includes one or more semantic components and one or more emotional components derived from the emotional state of the user. The emotional component(s) of the output can match the emotional state of the user or contrast with the emotional state of the user, among other possibilities. The VPA observes the behavior of the user in response to the synthesized output and then implements various modifications, based on the observed behavior, to improve the effectiveness of future interactions with the user.

At least one technical advantage of the disclosed techniques relative to the prior art is that the disclosed techniques enable a VPA to more accurately determine one or more operations to perform on behalf of the user based on the emotional state of the user. Accordingly, when implemented within a vehicle, the disclosed VPA helps to prevent the user from diverting attention away from driving in order to interact with vehicle features, thereby increasing overall driving safety. Another technical advantage of the disclosed techniques is that the disclosed techniques enable a VPA to generate conversationally-realistic responses that attempt to reflect the emotional state of the user. Conversationally-realistic responses maintain user engagement with the VPA and, therefore, reduce the number of situations where a user turns off the VPA and interacts with vehicle features manually, which increases overall driving safety. These technical advantages represent one or more technological advancements over prior art approaches.

System Overview

Figure 1A:
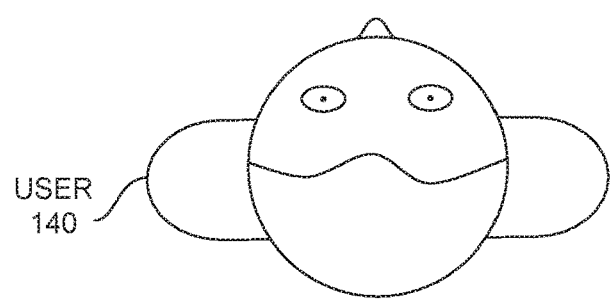
Figure 1B:
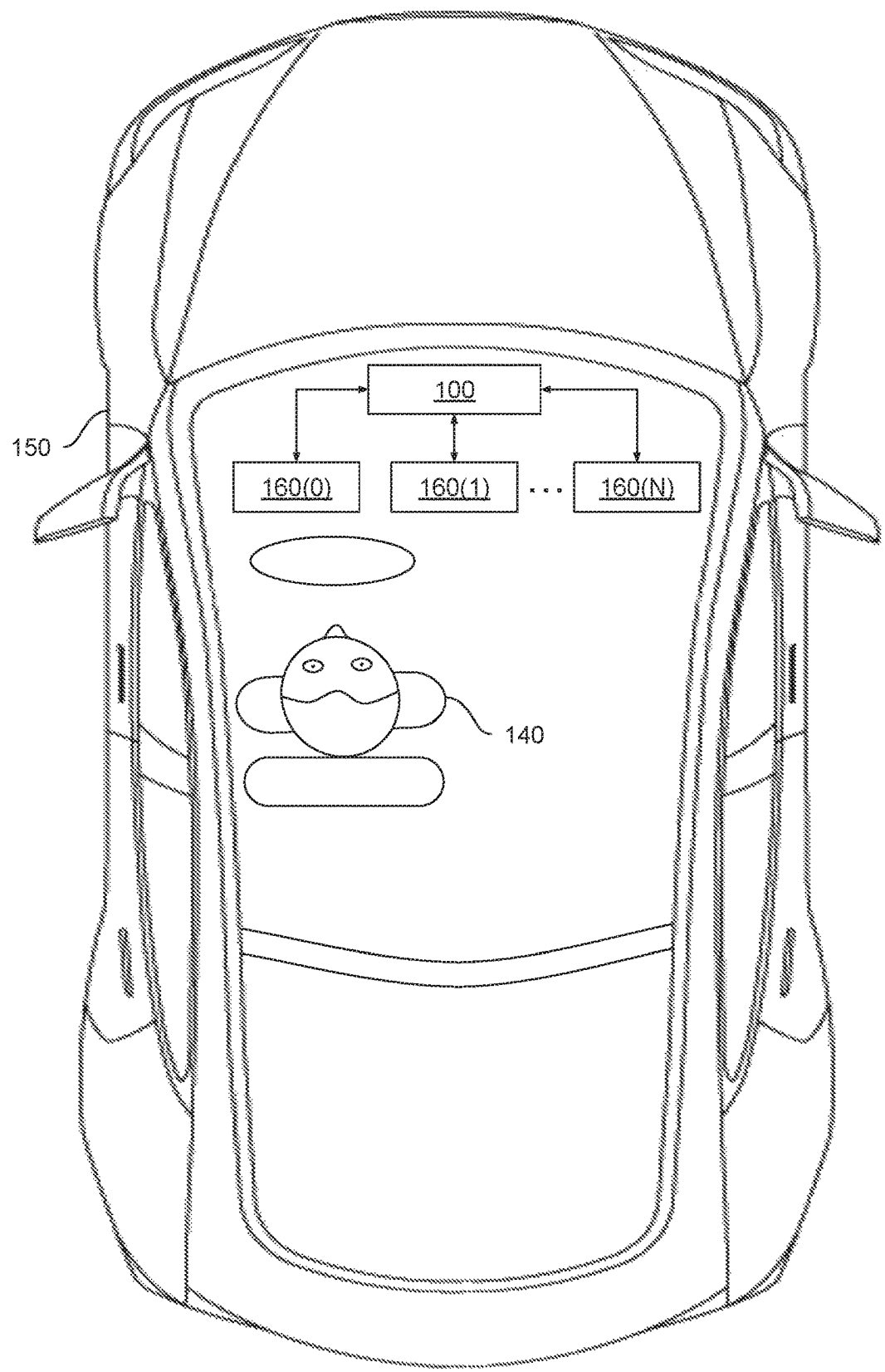

FIGS. 1A-1B illustrate a system configured to implement one or more aspects of the various embodiments. As shown in FIG. 1A, a system 100 includes a computing device 110 coupled to one or more input devices 120 and one or more output devices 130.

Input devices 120 are configured to capture input 122 that reflects one or more behaviors associated with a user 140. As referred to herein, a "behavior" includes any voluntary and/or involuntary actions performed by the user. For example, and without limitation, a "behavior" could include explicit commands issued by the user, facial expressions enacted by the user, changes in affect presented consciously or unconsciously by the user, as well as changes in user posture, heart rate, skin conductivity, pupil dilation, and so forth. Input devices 120 may include a wide variety of different types of sensors that are configured to capture different types of data that reflect behaviors associated with the user. For example, and without limitation, input devices 120 could include audio capture devices that record vocalizations issued by the user, optical capture devices that record images and/or video depicting the user, pupillometry sensors that measure the pupil dilation of the user, infrared sensors that measure blood flow in the face and/or body of the user, heart rate sensors that generate a beats-per-minute reading associated with the user, galvanic skin response sensors that measure changes in skin conductivity of the user, body temperature sensors that detect changes in the core and/or surface body temperature of the user, brainwave sensors that detect different brainwave patterns, and so forth. As described in greater detail below, computing device 110 processes input 122 to generate output 132.

Output devices 130 are configured to transmit output 132 to user 140. Output 132 can include any technically feasible type of data associated with any given sensory modality, although in practice output devices 130 generate and transmit audio output to user 140. As such, output devices 130 generally include one or more audio output devices. For example, and without limitation, audio devices 130 could include one or more speakers, one or more acoustic transducers, a set of headphones, a beamforming array, an acoustic field generator, and/or a sound cone.

Computing device 110 may be any technically feasible type of computer system, including a desktop computer, a laptop computer, a mobile device, a virtualized instance of a computing device, a distributed and/or cloud-based computer system. Computing device 110 includes a processor 112, input/output (I/O) devices 114, and a memory 116, coupled together. Processor 112 includes any technically feasible set of hardware units configured to process data and execute software applications. For example, and without limitation, processor 112 could include one or more central processing units (CPUs), one or more graphics processing units (GPUs), and/or one or more application-specific integrated circuits (ASICs). I/O devices 114 include any technically feasible set of devices configured to perform input and/or output operations. For example, and without limitation, I/O devices 114 could include a universal serial bus (USB) port, a serial port, and/or a firewire port. In one embodiment, I/O devices 114 may include input devices 120 and/or output devices 130. Memory 116 includes any technically feasible storage media configured to store data and software applications. For example, and without limitation, memory 116 could include a hard disk, a random-access memory (RAM) module, and/or a read-only memory (ROM). Memory 116 includes a virtual private assistant (VPA) 118. VPA 118 is a software application that, when executed by processor 112, performs various operations based on input 122 to generate output 132.

In operation, VPA 118 processes input 122 captured via input devices 120 and determines the emotional state of user 140 based on that input. VPA 118 also determines one or more operations to perform on behalf of user 140 based on input 122 and the determined emotional state. VPA 118 determines the emotional state of user 140 and the one or more operations to perform on behalf of user 140 using techniques described in greater detail below in conjunction with FIGS. 2-3B. VPA 118 then executes the one or more operations or causes the one or more operations to be executed by another system. VPA 118 synthesizes output 132 based on the emotional state of user 140 and the one or more operations. The synthesized output includes semantic components related to the one or more operations and emotional components derived from and/or influenced by the emotional state of the user. VPA 118 transmits output 132 to user 140 via output devices 130. VPA 118 observes the behavior of user 140 in response to the synthesized output and then implements various modifications that can increase usability of and/or user engagement with VPA 118.

As a general matter, system 100 may be implemented as a stand-alone system or be integrated with and/or configured to interoperate with any other technically feasible system. For example, and without limitation, system 100 could be integrated with and/or configured to interoperate with a vehicle, a smart home, a smart headphone, a smart speaker, a smart television set, one or more Internet-of-Things (IoT) devices, or a wearable computing system, among others. FIG. 1B illustrates an exemplary implementation where system 100 is integrated with a vehicle.

As shown in FIG. 1B, system 100 is integrated with a vehicle 150 where user 140 resides. System 100 is coupled to one or more subsystems 160(0) through 160(N) within that vehicle. Each subsystem 160 provides access to one or more vehicle features. For example, and without limitation, a given subsystem 160 could be a climate control subsystem that provides access to climate control features of the vehicle, an infotainment subsystem that provides access to infotainment features of the vehicle, a navigation subsystem that provides access to navigation features of the vehicle, an autonomous driving subsystem that provides access to autonomous driving features of the vehicle, and so forth. VPA 118 within system 100 is configured to access one or more subsystems 160 in order to execute operations on behalf of user 140.

Referring generally to FIGS. 1A-1B, persons skilled in the art will understand that system 100 in general and VPA 118 in particular can be implemented in any technically feasible environment in order to perform operations on behalf of user 140 and to synthesize vocalizations based on the emotional state of user 140. Various examples of devices that can implement and/or include VPAs include mobile devices (e.g., cellphones, tablets, laptops, etc.), wearable devices (e.g., watches, rings, bracelets, headphones, AR/VR head mounted devices, etc.), consumer products (e.g., gaming, gambling, etc.), smart home devices (e.g., smart lighting systems, security systems, smart speakers, etc.), communications systems (e.g., conference call systems, video conferencing systems, etc.), and so forth. VPAs may be located in various environments including, without limitation, road vehicle environments (e.g., consumer car, commercial truck, ride hailing vehicles, snowmobiles, all-terrain vehicles (ATVs), semi and fully autonomous vehicles, etc.), aerospace and/or aeronautical environments (e.g., airplanes, helicopters, spaceships, electric vertical takeoff and landing aircraft (eVTOLs), etc.), nautical and submarine environments (e.g., boats, ships, jet skis), and so forth. Various modules that implement the overarching functionality of VPA 118 are described in greater detail below in conjunction with FIG. 2.

Software Overview

Figure 2:
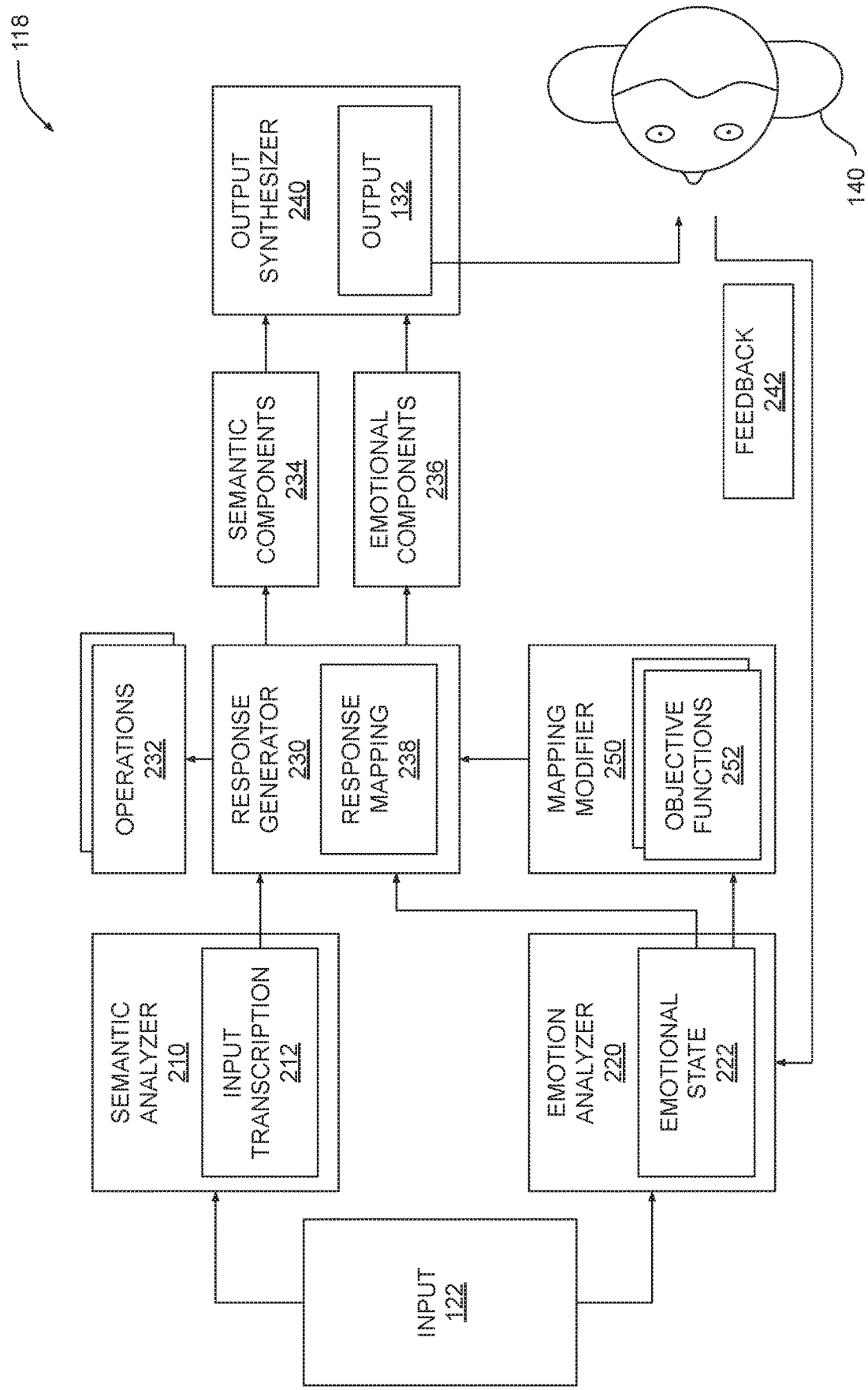
FIG. 2 is a more detailed illustration of the VPA of FIG. 1, according to various embodiments.

FIG. 2 is a more detailed illustration of the VPA of FIG. 1, according to various embodiments. As shown, VPA 118 includes a semantic analyzer 210, an emotion analyzer 220, a response generator 230, an output synthesizer 240, and a mapping modifier 250. These various elements are implemented as software and/or hardware modules that interoperate to perform the functionality of VPA 118.

In operation, semantic analyzer 210 receives input 122 from user 140 and performs a speech-to-text transcription operation on vocalizations included in that input to generate input transcription 212. Input transcription 212 includes textual data that reflects commands, questions, statements, and other forms of linguistic communication that user 140 issues to VPA 118 in order to elicit a response from VPA 118. For example, and without limitation, input transcription 212 could include a command indicating an operation that user 140 wants VPA 118 to perform. Input transcription 212 could also indicate a question that user 140 wants VPA 118 to answer or a statement that user 140 makes to VPA 118. Semantic analyzer 210 transmits input transcription 212 to response generator 230.

Emotion analyzer 220 also receives input 122 from user 140 and then performs an emotional analysis operation on input 122 in order to determine an emotional state 222 associated with user 140. Emotion analyzer 220 may also determine emotional state 222 based on input transcription 212. Emotion analyzer 220 can perform any technically feasible approach to characterizing the emotional state of a living entity when generating emotional state 222 and in doing so may process any technically feasible form of data included within input 122. For example, and without limitation, emotion analyzer 220 could process a vocalization received from user to quantify the pitch, tone, timbre, volume, and/or other acoustic features of that vocalization. Emotion analyzer 220 could then map those features to a specific emotional state or emotional metric. In another example, without limitation, emotion analyzer 220 could process a video of a facial expression enacted by user 140 and then classify that facial expression as corresponding to a particular emotional state. In one embodiment, emotional state 222 may include a valence value indicating a particular type of emotion and an intensity value indicating an intensity with which that type of emotion is expressed and/or an arousal level corresponding to that type of emotion, as also described below in conjunction with FIGS. 3A-3B. Persons skilled in the art will understand that emotion analyzer 220 can implement any technically feasible approach for characterizing emotions and can generate emotional state 222 to include any technically feasible data that describes emotions. Emotion analyzer 220 transmits emotional state 222 to response generator 230.

Response generator 230 is configured to process input transcription 212 and emotional state 222 in order to generate operations 232. Each operation 232 may correspond to a command that is received from user 140 and included within input transcription 212. VPA 118 can execute a given operation 232 in response to a given command on behalf of user 140 or offload that operation to another system to be executed on behalf of user 140. For example, and without limitation, VPA 118 could offload a given operation 232 to one of the vehicle subsystems 160 shown in FIG. 1B. In one embodiment, response generator 230 may generate a set of eligible operations based on input transcription 212 and then select a subset of those operations to execute based on emotional state 222.

Response generator 230 is further configured to process input transcription 212 and emotional state 222 in order to generate semantic components 234. Semantic components 234 include textual data that is synthesized into output 132 and subsequently transmitted to user 140, as further described below. Semantic components 234 can include words, phrases, and/or sentences that are contextually relevant to input transcription 212. For example, and without limitation, semantic components 234 could include an acknowledgement that a command was received from user 140. Semantic components 234 can also describe and/or reference operations 232 and/or the status of executing those operations. For example, and without limitation, semantic components 234 could include an indication that a specific operation 232 was initiated in response to a command received from user 140.

Response generator 230 is also configured to process input transcription 212 and emotional state 222 in order to generate emotional components 236. Emotional components 236 indicate specific emotional qualities and/or attributes that are derived from emotional state 222 and incorporated into output 132 during synthesis. For example, and without limitation, a given emotional component 236 could include a specific pitch, tone, timbre, volume, diction speed, and/or annunciation level with which the vocalization should be synthesized to reflect particular emotional qualities and/or attributes.

In various embodiments, response generator 230 is configured to generate voice responses that, although having the same or similar semantic content, can vary based on various speech levels, such as (i) overall tempo, loudness, and pitch of the synthesized voice, (ii) vocal affect parameters which will be explained in more detail below, (iii) non-verbal and non-language vocalizations, paralinguistic respiration (e.g., laugh, cough, whistles, etc.), and (iv) non-speech altering sounds (e.g., beeps, chirps, clicks, etc.). These voice responses vary in their perceived emotional effect, e.g., the same semantic content can be rendered with speech that appears soft and sweeping to the user, or rash and abrupt. These variations in perceived emotional effect may be generated by using words with soft vs. hard sounds, and polysyllabic vs. abrupt rhythms. For example, sounds such as "l," "m," and "n," and long vowels or diphthongs, reinforced by a gentle polysyllabic rhythm, are interpreted as "nicer" than words with hard sounds such as "g" and "k," short vowels, and an abrupt rhythm. The field of Sound Symbolism (as described in, for example, http://grammar.about.com/od/rs/g/soundsymbolismterm.htm) provides a variety of heuristics that attempt to instill affect by connecting particular sound sequences with particular meanings in speech. The vocal affect parameters as noted above generally include (i) pitch parameters (e.g., accent shape, average pitch, contour slope, final lowering, and pitch range), (ii) timing parameters (e.g., speech rate and stress frequency), (iii) voice quality parameters (e.g., breathiness, brilliance, laryngealization, loudness, pause discontinuity, and pitch continuity), and (iv) articulation parameters. The voice output may also include, other than audible speech, non-linguistic vocalizations such as laughter, breathing, hesitation (e.g., "uhm"), and/or non-verbal consent (e.g., "aha")

In some instances, a given emotional component 236 can be complementary to or aligned with emotional state 222. For example, and without limitation, if emotional state 222 indicates that user 140 is currently "happy," then emotional components 236 could include a specific tone of voice commonly associated with "happiness." Conversely, a given emotional component 236 can diverge from emotional state 222. For example, and without limitation, if emotional state 222 indicates that user 140 is currently "angry," then emotional components 236 could include a specific tone of voice commonly associated with "calmness." FIGS. 3A-3B set forth various examples of how response generator 230 generates emotional components 236 based on emotional state 222.

In one embodiment, response generator 230 may implement a response mapping 238 that maps input transcription 212 and/or emotional state 222 to one or more operations 232, one or more semantic components 234, and/or one or more emotional components 236. Response mapping 238 may be any technically feasible data structure based on which one or more inputs can be processed to generate one or more outputs. For example, and without limitation, response mapping 238 could include an artificial neural network, a machine learning model, a set of heuristics, a set of conditional statements, and/or one or more look-up tables, among others. In various embodiments, response mapping 238 may be obtained from a cloud-based repository of response mappings that are generated for different users by different instances of system 100. Further, response mapping 238 may be modified using techniques described in greater detail below and then uploaded to the cloud-based repository for use in other instances of system 100.

Response generator 230 transmits semantic components 234 and emotional components 236 to output synthesizer 240. Output synthesizer 240 is configured to combine semantic components 234 and emotional components 236 to generate output 132. Output 132 generally takes the form of a synthetic vocalization. Output synthesizer 132 transmits output 132 to user 140 via output devices 130. With the above techniques, VPA 118 uses the emotional state of user 140 in order to more effectively interpret inputs received from user 140 and to more effectively generate vocalizations in response to user 140. In addition, VPA 118 can adapt based on the response of user 140 to a given output 132 in order to improve usability and engagement with user 140.

In particular, VPA 118 is configured to capture feedback 242 that reflects one or more behaviors user 140 performs in response to output 132. VPA 118 then updates emotional state 222 to reflect any observed behavioral changes in user 140. Mapping modifier 250 evaluates one or more objective functions 252 based on the updated emotional state 222 to quantify the effectiveness of output 132 in causing specific types of behavioral changes in user 140. For example, and without limitation, a given objective function 252 could quantify the effectiveness of mapping a given input transcription 212 to a particular set of operations 232 based on whether emotional state 222 indicates that user 140 is pleased or displeased. In another example, without limitation, a given objective function could quantify the effectiveness of selecting specific semantic components 234 when generating output 132 based on whether emotional state 222 indicates interest or disinterest. In yet another example, without limitation, a given objective function 252 could quantify the effectiveness of incorporating "soothing" tones into output 132 to calm user 140 when user 140 occupies a "nervous" emotional state.

As a general matter, a given objective function 252 can represent a target behavior for user 140, a target emotional state 222 for user 140, a target state of being of user 140, a target level of engagement with VPA 118, or any other technically feasible objective that can be evaluated based on feedback 242. In embodiments where response generator 230 includes response mapping 238, mapping modifier 250 may update response mapping 238 in order to improve subsequent outputs 132. In the manner described, VPA 118 can adapt to the specific personalities and idiosyncrasies of different users and therefore improve over time at interpreting and engaging with user 140.

Exemplary Characterization and Translation of Emotional States

Figure 3A:
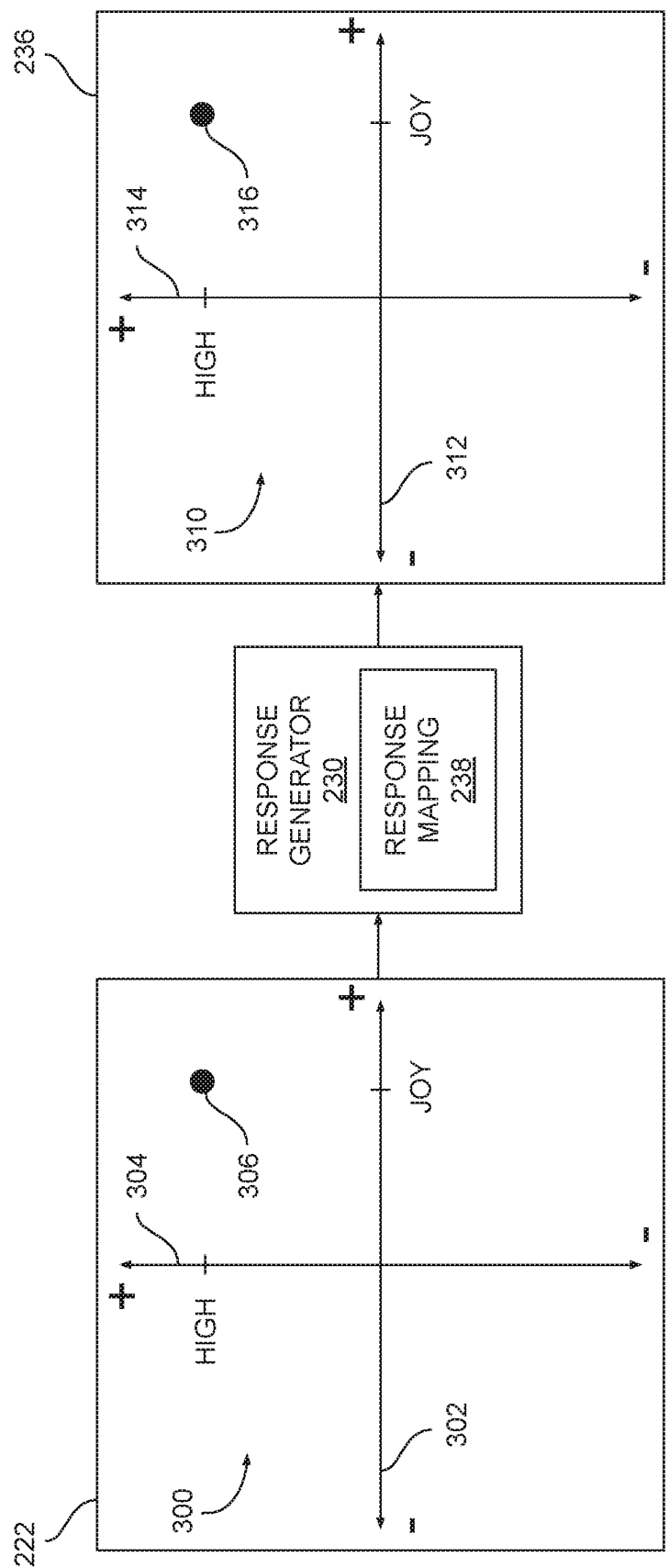
FIGS. 3A-3B set forth examples of how the VPA of FIG. 1 characterizes and translates the emotional state of a user, according to various embodiments.
Figure 3B:
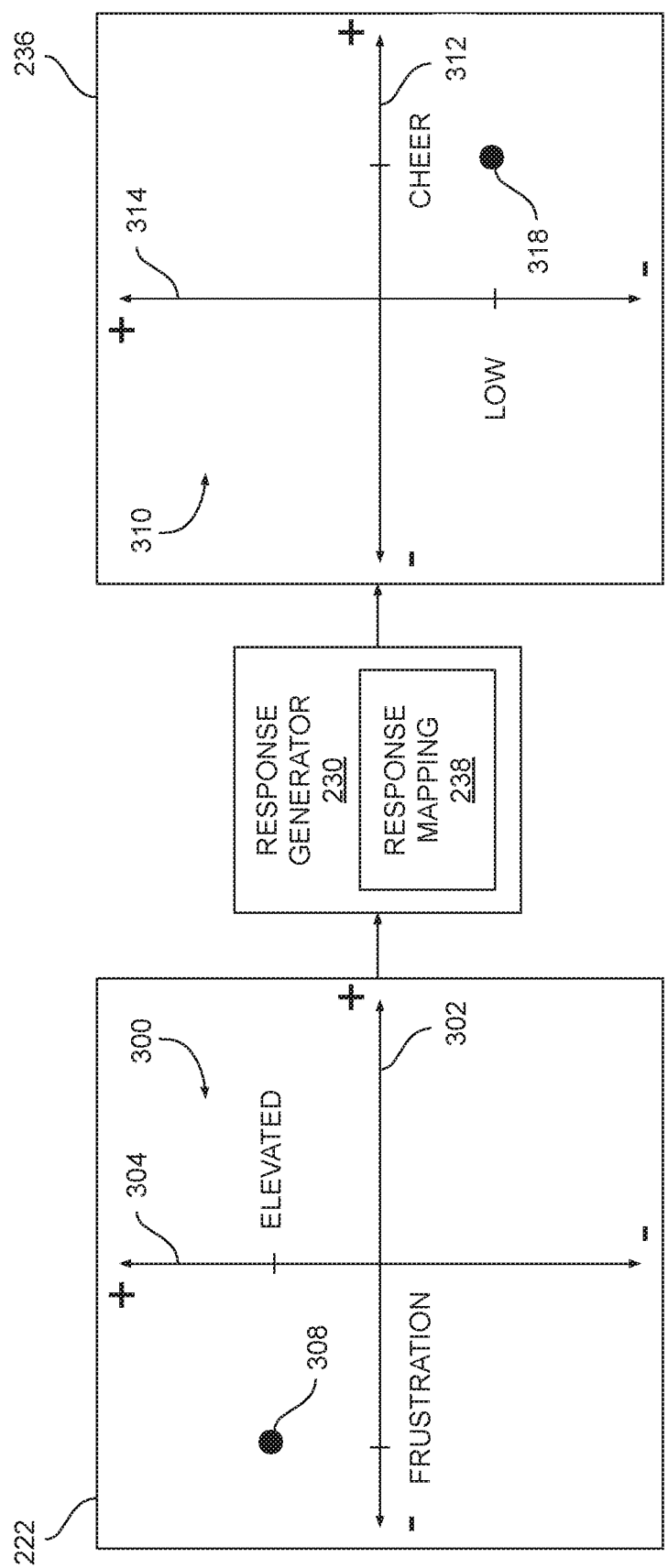

FIGS. 3A-3B set forth examples of how the VPA of FIG. 1 characterizes and translates the emotional state of a user, according to various embodiments. As shown in FIG. 3A, emotional state 222 is defined using a graph 300 that includes a valence axis 302, an intensity axis 304, and a location 306 plotted against those two axes. Valence axis 302 defines a spectrum of locations that may correspond to different types of emotions, such as "joy," "happiness," "anger," and "excitement," among others. Intensity axis 304 defines a range of intensities corresponding to each type of emotion. Location 306 corresponds to a particular type of emotion set forth via valence axis 302 and a particular intensity with which that emotion is expressed. In the example shown, location 306 corresponds to a high level of joy.

Emotion analyzer 220 generates emotional state 222 based on any of the different types of analyses described previously. Response generator 230 then generates emotional component 236 that similarly defines a graph 310 that includes a valence axis 312 and an intensity axis 314. Graph 310 also includes location 316 that represents the emotional qualities to be included in output 132 during synthesis. In the example shown, location 316 corresponds to a high level of joy, similar to location 306, and output 132 is therefore generated with emotional qualities that are meant to compliment emotional state 222 of user 140. Response generator 230 can also generate emotional components 236 that differ from emotional state 222, as shown in FIG. 3B.

Referring now to FIG. 3B, emotional state 222 includes location 308 that corresponds to an elevated level of frustration. Response generator 230 generates emotional component 236 to include location 318 that corresponds to a low level of cheer. Output 132 is therefore generated with emotional qualities that differ from emotional state 222 but can potentially modify that emotional state by reducing the frustration of user 140 via cheerful vocalizations.

Referring generally to FIGS. 3A-3B, in various embodiments, response generator 230 may implement response mapping 238 in order to map specific locations on graph 300 to other locations on graph 310, thereby achieving the different types of translations between emotional states 222 and emotional components 236 described by way of example above. Persons skilled in the art will understand that VPA 118 can implement any technically feasible approach to characterizing emotional states and/or emotional components beyond the exemplary techniques described in conjunction with FIGS. 3A-3B.

As discussed, system 100 in general and VPA 118 in particular can be integrated into a wide variety of different types of systems, including vehicles. FIGS. 4A-5C set forth exemplary scenarios where system 100 is integrated into a vehicle and the disclosed techniques enable greater usability, thereby preventing user 140 from needing to divert attention away from driving.

Exemplary VPA Interactions

Figure 4A:
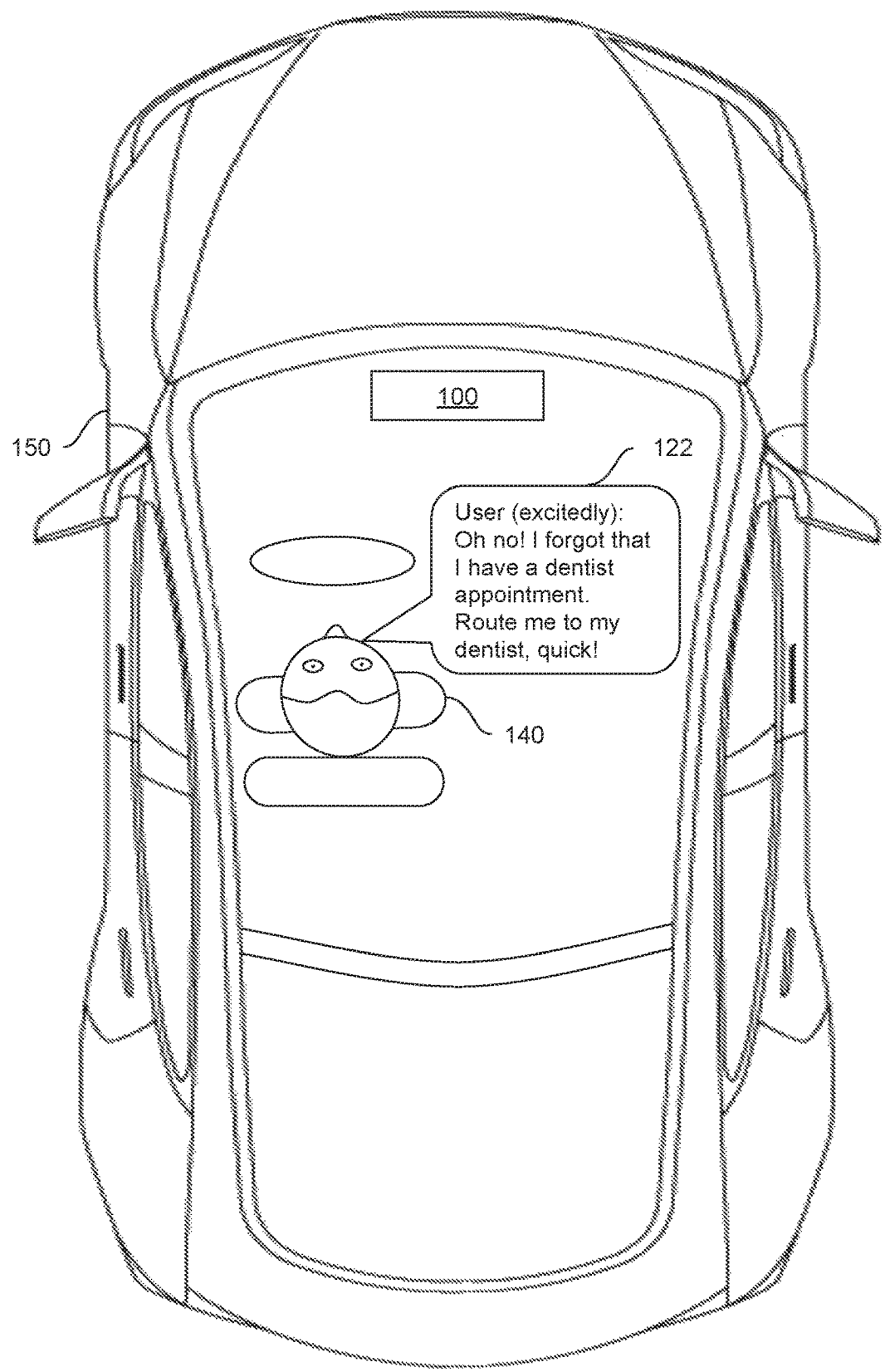
FIGS. 4A-4C set forth an example of how the VPA of FIG. 1 responds to the emotional state of a user, according to various embodiments.
Figure 4B:
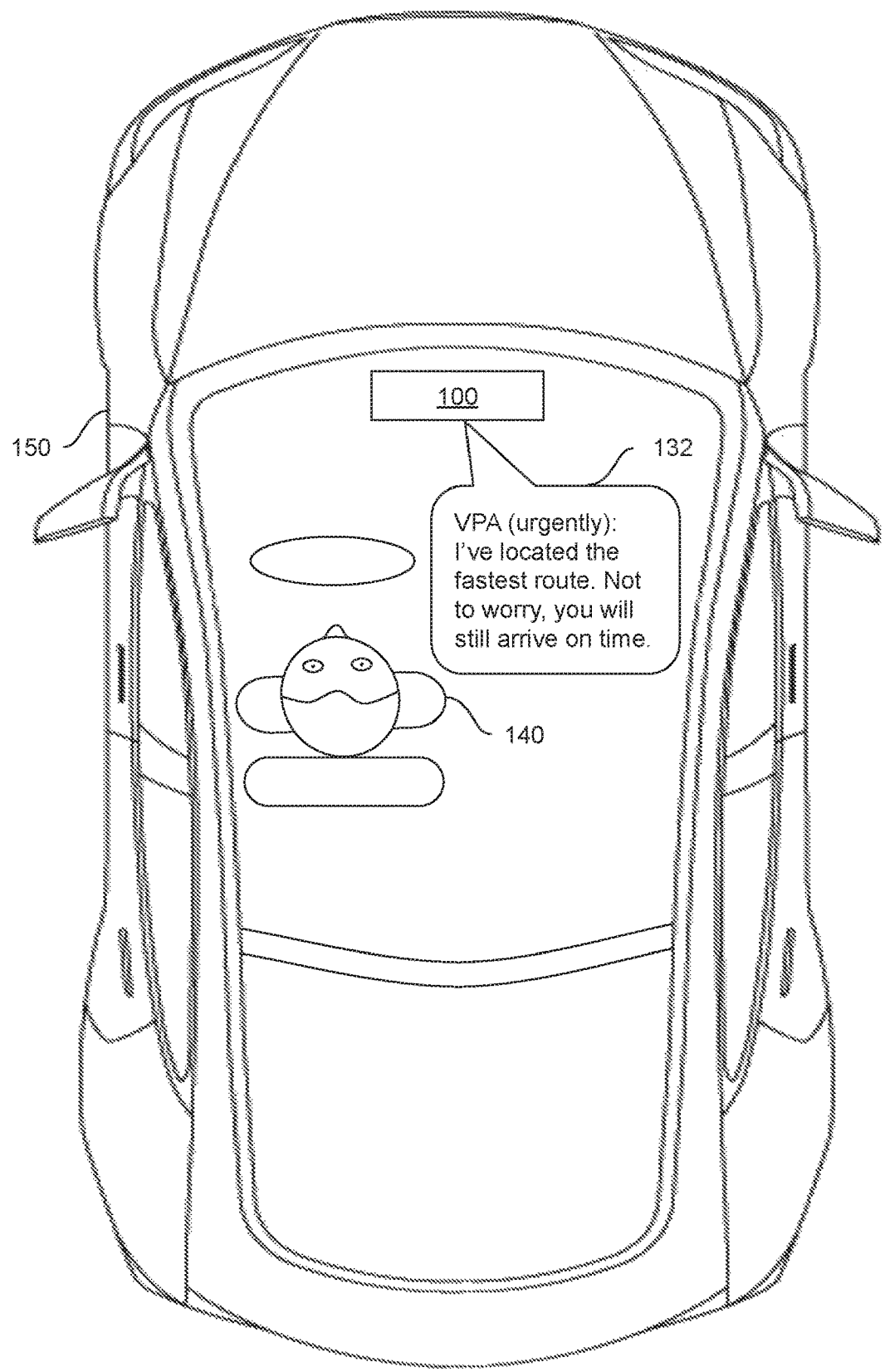
Figure 4C:
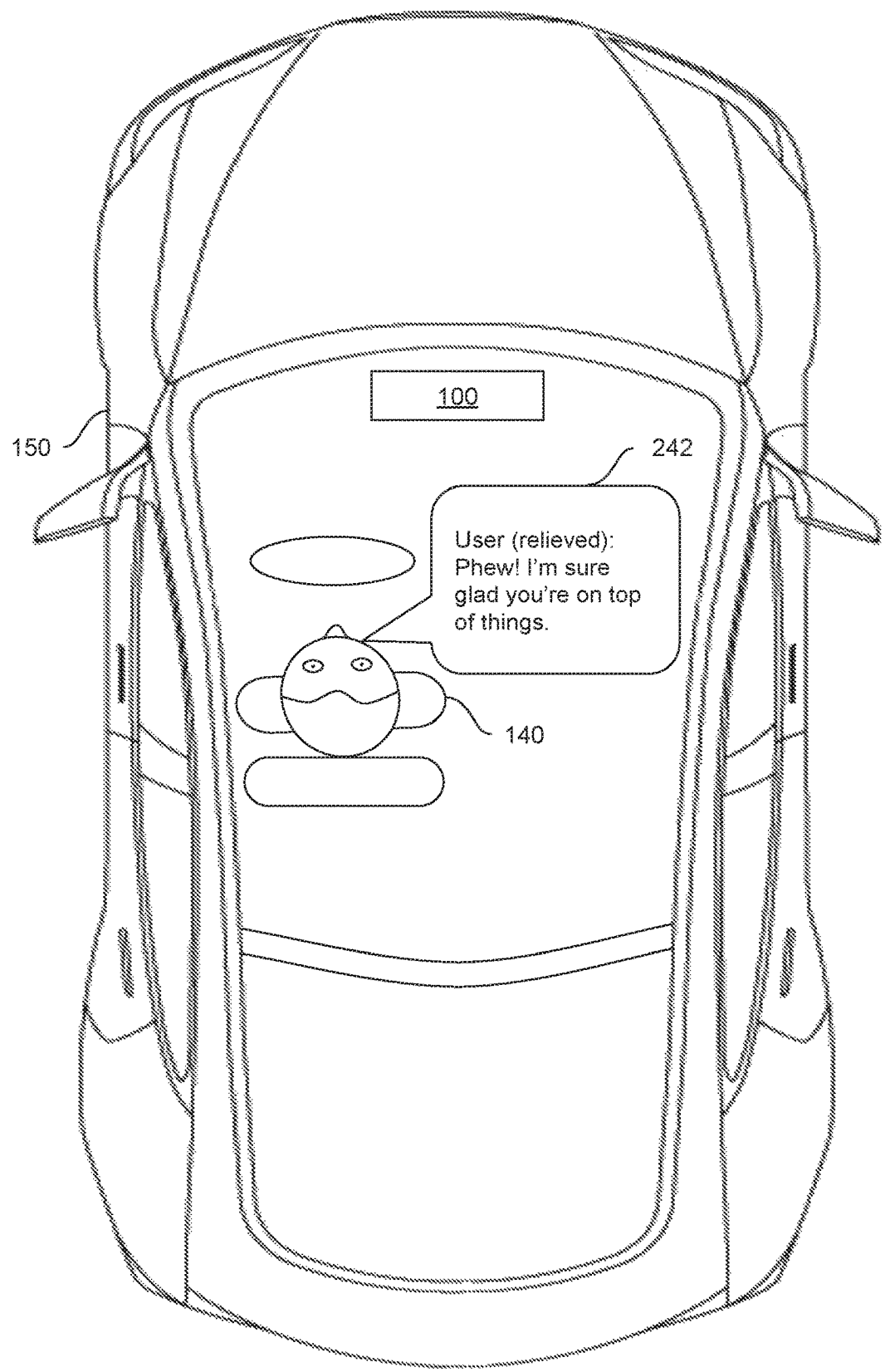

FIGS. 4A-4C set forth an example of how the VPA of FIG. 1 responds to the emotional state of a user, according to various embodiments. As shown in FIG. 4A, system 100 is integrated within vehicle 150 where user 140 resides, as also shown in FIG. 1B. User 140 excitedly exclaims how they forgot about a dentist appointment and asks that VPA 118 (within system 100) quickly provide a route to the dentist. VPA 118 analyzes input 122 and detects specific vocal characteristics commonly associated with feelings of excitement and/or anxiety. As shown in FIG. 4B, VPA 118 then generates an output 132 that matches the detected level of excitement. In particular, VPA 118 urgently states that the fastest route has been located and then reassures user 140 that they will arrive in a timely manner. Subsequently, as shown in FIG. 4C, user 140 expresses relief, which VPA 118 processes as feedback 242 in order to inform future interactions with user 140. In this example, VPA 118 facilitates user engagement by appearing emotionally responsive to user 140, thereby encouraging user 140 to continue using VPA 118 instead of personally performing various vehicle-oriented operations.

Figure 5A:
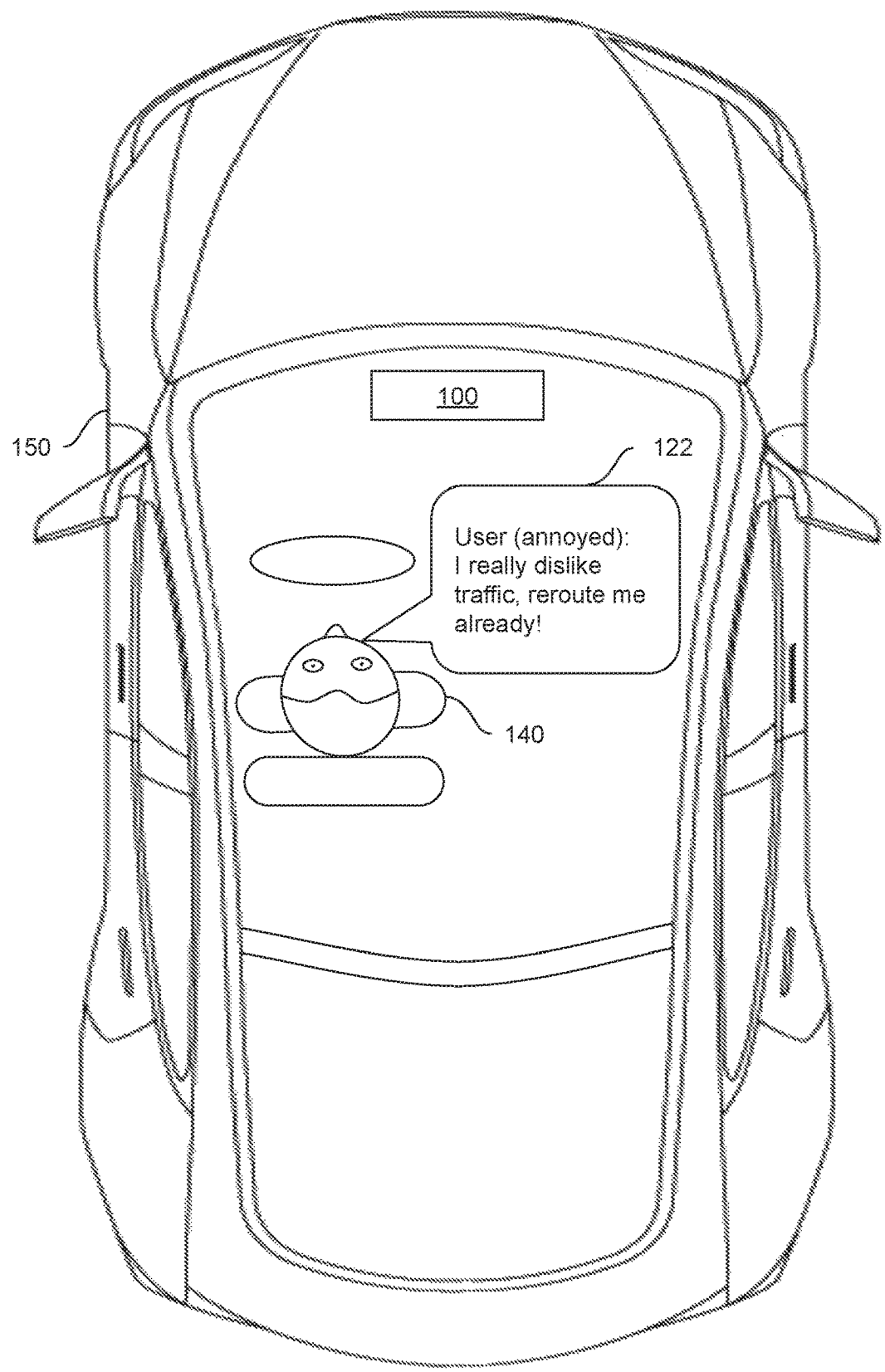
FIGS. 5A-5C set forth an example of how the VPA of FIG. 1 compensates for the emotional state of a user, according to various embodiments.
Figure 5B:
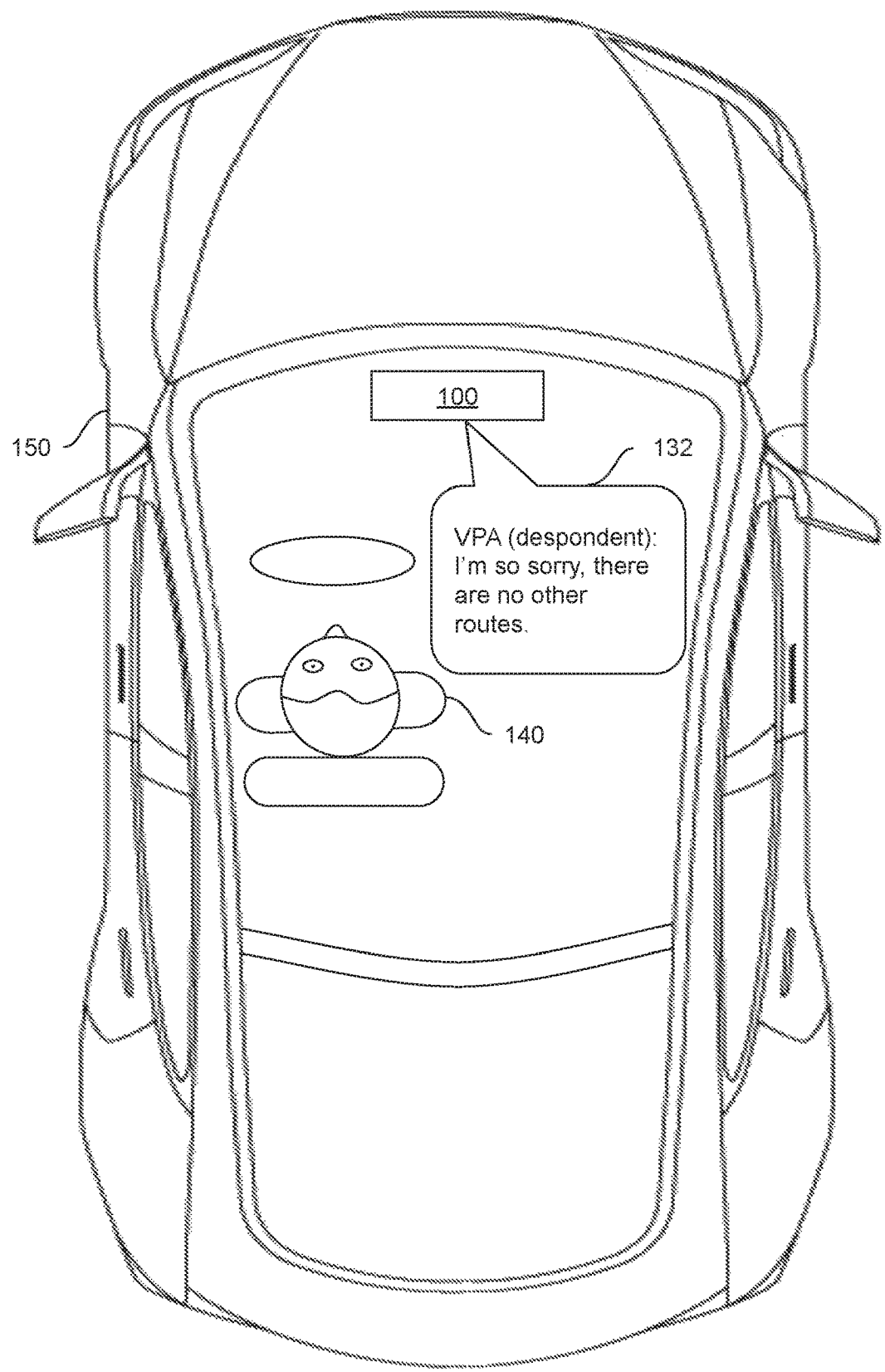
Figure 5C:
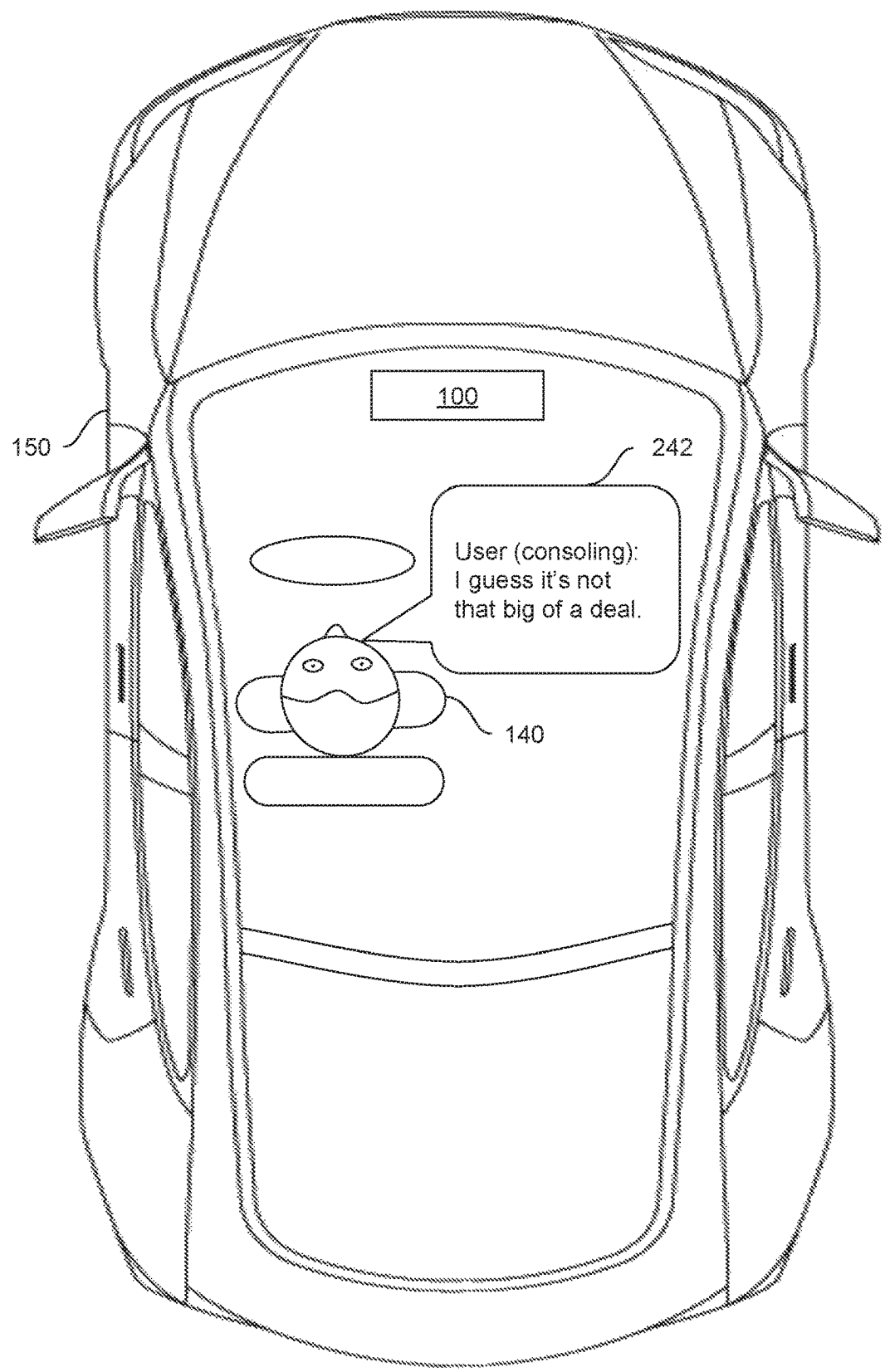

FIGS. 5A-5C set forth an example of how the VPA of FIG. 1 compensates for the emotional state of a user, according to various embodiments. In this example, VPA 118 implements emotional components that are different from the emotional state of user 140 in order to effect a change in the emotional state of user 140. As shown in FIG. 5A, user 140 expresses annoyance at having to drive in traffic. VPA 118 analyzes input 122 and detects specific vocal characteristics commonly associated with feelings of annoyance and/or frustration. As shown in FIG. 5B, VPA 118 then generates an output 132 with emotional qualities markedly different from these particular feelings. Specifically, VPA 118 despondently apologies and admits that there are no other routes available. Subsequently, as shown in FIG. 4C, user 140 forgets the previous feelings of annoyance and provides consolation to VPA 118, which VPA 118 processes as feedback 242 in order to inform future interactions with user 140. In this example, VPA 118 facilitates user engagement by appearing emotionally sensitive to user 140, thereby encouraging user 140 to continue using VPA 118 instead of personally performing various vehicle-oriented operations.

Procedure for Performing Operations in Response to User Emotional State

Figure 6:
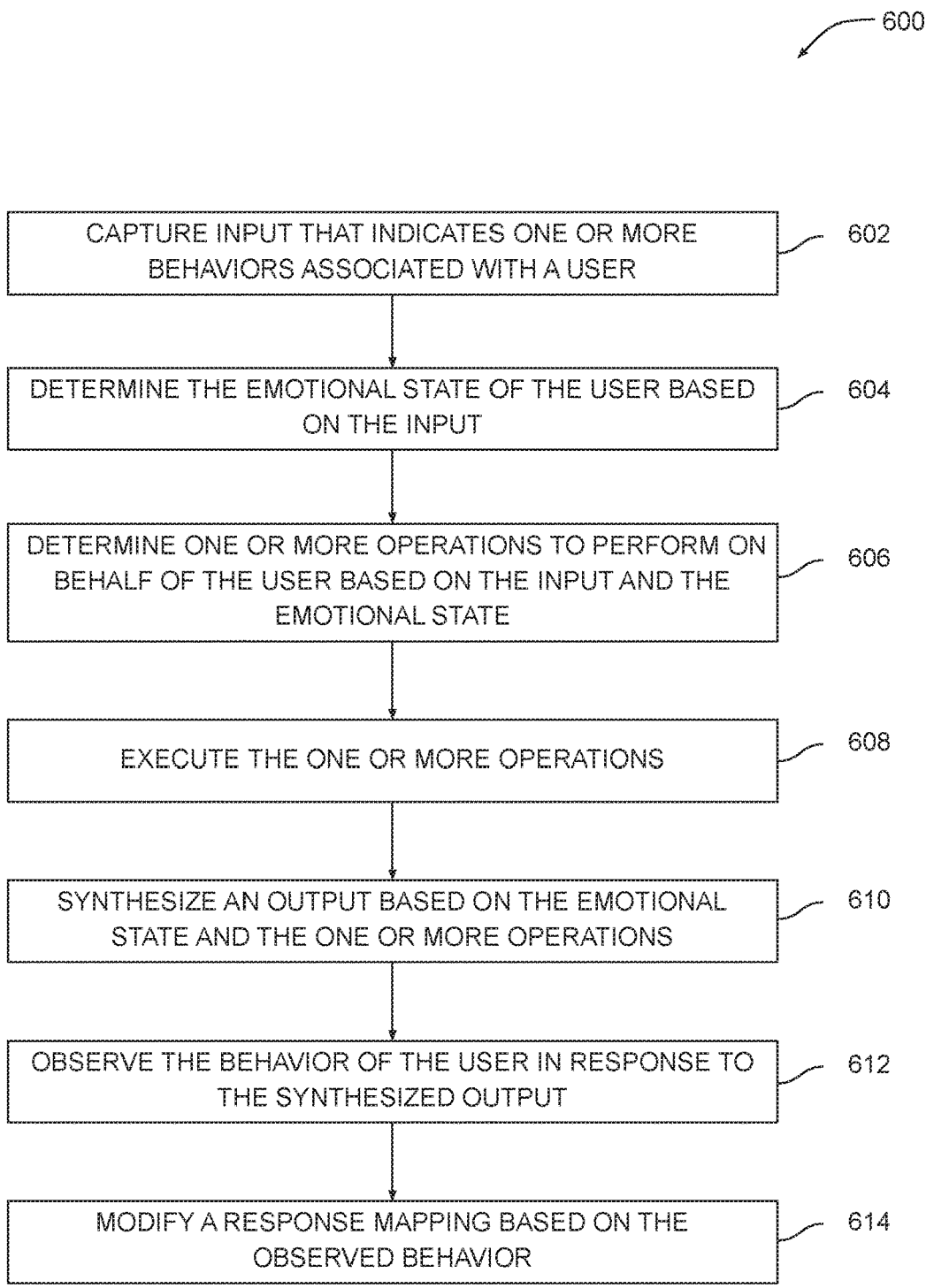
FIG. 6 is a flow diagram of method steps for synthesizing vocalizations that reflect the emotional state of a user, according to various embodiments.

FIG. 6 is a flow diagram of method steps for synthesizing vocalizations that reflect the emotional state of a user, according to various embodiments. Although the method steps are described in conjunction with the systems of FIGS. 1-5C, persons skilled in the art will understand that any system configured to perform the method steps in any order falls within the scope of the present embodiments.

As shown, a method 600 begins at step 602, where VPA 118 captures an input that indicates one or more behaviors associated with a user. VPA 118 interacts with input devices 120 shown in FIG. 1 to capture the input. Input devices 120 may include a wide variety of different types of sensors that are configured to capture different types of data associated with the user, including audio capture devices that record vocalizations issued by the user, optical capture devices that record images and/or video depicting the user, pupillometry sensors that measure the pupil dilation of the user, infrared sensors that measure blood flow in the face and/or body of the user, heart rate sensors that generate a beats-per-minute reading associated with the user, galvanic skin response sensors that measure changes in skin conductivity of the user, body temperature sensors that detect changes in the core and/or surface body temperature of the user, brainwave sensors that detect different brainwave patterns, and so forth. Any and all such data can be processed to determine the emotional state of the user, as described in greater detail below.

At step 604, VPA 118 determines the emotional state of the user based on the input. In doing so, VPA 118 implements emotion analyzer 220 to process any of the above types of data in order to map that data and/or processed versions thereof to the emotional state of the user. Emotion analyzer 220 can define the emotional state of the user using any technically feasible approach. In one embodiment, emotion analyzer 220 may describe the emotional state of the user via a valence versus intensity dataset, such as that shown in FIGS. 3A-3B. In particular, emotion analyzer 220 analyzes specific qualities associated with the input, such as the pitch, timbre, tone, and/or volume associated with user vocalizations, among others things, and then maps those qualities to a particular location within a multidimensional valence versus intensity space. Persons skilled in the art will understand that VPA 118 can implement any technically feasible approach to generating data that indicates the emotional state of the user when performing step 604.

At step 606, VPA 118 determines one or more operations to perform on behalf of the user based on the input captured at step 602 and the emotional state determined at step 604. VPA 118 implements response generator 230 in order to process a transcription of the input to determine one or more relevant operations to perform on behalf of the user. For example, if the input corresponds to a command to play music, then VPA 118 could process a transcription of the input and then activate the stereo system within a vehicle where the user resides. VPA 118 can implement any technically feasible approach to generating transcriptions of input, including speech-to-text, among other approaches. In some embodiments, response generator 230 can also select a relevant set of operations to perform based on the emotional state of the user determined at step 606. For example, if user occupies a "sad" emotional state, then VPA 118 could select a particular radio station that plays somber music.

At step 608, VPA 118 executes the one or more operations on behalf of the user in order to assist the user in performing those operations. In some embodiments, VPA 118 may execute the one or more operations by executing one or more corresponding subroutines and/or software functions. In other embodiments, VPA 118 may be integrated with another system, and VPA executes the one or more operations by causing that system to perform those operations. For example, with implementations where VPA 118 is integrated into a vehicle, as described above, VPA 118 could execute a given operation to cause one or more subsystems within the vehicle to perform the given operation. In such implementations, VPA 118 advantageously executes operations associated with the vehicle on behalf of the user and therefore prevents the user from having to divert attention away from driving to personally perform those operations.

At step 610, VPA 118 synthesizes an output based on the emotional state determined at step 604 and the one or more operations determined at step 606. VPA 118 implements response generator 230 in order to generate semantic components of the output as well as emotional components of that output. The semantic components of the output include one or more words, phrases, and/or sentences that relate in a meaningful way to the one or more operations. For example, if a given operation pertains to a set of navigation instructions for navigating a vehicle, then the semantic components of the output could include language associated with a first navigation instruction. In one embodiment, response generator 230 may generate the semantic components of the output to have emotive characteristics derived from the emotional state of the user. The emotional components of the output may indicate variations in pitch, tone, timbre, and/or volume that are derived from the emotional state of the user and that are meant to evoke a specific emotional response from the user. The emotional components of the output may also include other factors that influence how the semantic components of the output are conveyed to the user, such as the speed of delivery, timing, and so forth. Based on the semantic components and emotional components, output synthesizer 240 generates the output and transmits the output to the user via output devices 130.

At step 612, VPA 118 observes the behavior of the user in response to the output synthesized at step 610. VPA 118 captures any of the above-mentioned types of data that describe various behaviors associated with the user in order to determine how the user responds to the output. In particular, emotion analyzer 220 can analyze any captured data to determine how the emotional state of the user changes in response to the output. For example, and without limitation, emotion analyzer 220 could determine that the user, who previously occupied a "frustrated" emotional state, shifted to a "relaxed" emotional state in response to an output that included "soothing" emotional components.

At step 614, VPA 118 modifies response generator 230 and/or response mapping 238 included therein based on the observed behavior. In one embodiment, VPA 118 may implement mapping modifier 250 in order to evaluate one or more objective functions 252 and determine whether response generator 230 and/or response mapping 238 should be modified. Each objective function 252 may reflect a target set of behaviors for the user, a target emotional state, a target state of being, and so forth. For example, and without limitation, objective functions 252 could quantify the well-being, connectedness, productivity, and/or enjoyment of the user, and mapping modifier 250 could adjust response mapping 238 to maximize one or more of these objectives. Mapping modifier 250 can evaluate each objective function 252 in order to determine the degree to which the observed behavior corresponds to a given target behavior and then modify response mapping 238 to increase the degree to which the user expresses the target behavior. VPA 118 can implement any technically feasible approach to quantifying the expression of a given behavior.

VPA 118 implements the method 600 in order to perform some or all of the various features described herein. Although in some instances VPA 118 is described in relation to in-vehicle implementations, persons skilled in the art will understand how the disclosed techniques confer specific advantages relative to the prior art in a wide range of technically feasible implementations. As a general matter, the disclosed techniques enable VPA 118 to interpret vocalizations received from users more effectively and more accurately and enable VPA 118 to generate more conversationally realistic response to users, thereby achieving significantly better usability compared to prior art approaches.

In sum, a virtual private assistant (VPA) is configured to analyze various types of input that indicate one or more behaviors associated with a user. The input may include vocalizations that represent explicit commands for the VPA to execute, emotional state derived from these vocalizations, as well as implicit non-verbal cues associated with the user, such as facial expressions and/or changes in posture, among others. The VPA determines the emotional state of the user based on the input. The VPA also determines one or more operations to perform on behalf of the user based on the input and the determined emotional state. The VPA then executes the one or more operations and synthesizes an output based on the emotional state of the user and the one or more operations. The synthesized output includes one or more semantic components and one or more emotional components derived from the emotional state of the user. The emotional component(s) of the output can match the emotional state of the user or contrast with the emotional state of the user, among other possibilities. The VPA observes the behavior of the user in response to the synthesized output and then implements various modifications, based on the observed behavior, to improve the effectiveness of future interactions with the user.

At least one technical advantage of the disclosed techniques relative to the prior art is that the disclosed techniques enable a VPA to more accurately determine one or more operations to perform on behalf of the user based on the emotional state of the user. Accordingly, when implemented within a vehicle, the disclosed VPA helps to prevent the user from diverting attention away from driving in order to interact with vehicle features, thereby increasing overall driving safety. Another technical advantage of the disclosed techniques is that the disclosed techniques enable a VPA to generate conversationally-realistic responses that attempt to reflect the emotional state of the user. Conversationally-realistic responses maintain user engagement with the VPA and, therefore, reduce the number of situations where a user turns off the VPA and interacts with vehicle features manually, which increases overall driving safety. These technical advantages represent one or more technological advancements over prior art approaches.

1. Some embodiments include a computer-implemented method for interacting with a user while assisting the user, the method comprising capturing a first input that indicates one or more behaviors associated with the user, determining a first emotional state of the user based on the first input, generating a first vocalization that incorporates a first emotional component based on the first emotional state, wherein the first vocalization relates to a first operation that is being performed to assist the user, and outputting the first vocalization to the user.

2. The computer-implemented method of clause 1, wherein the user resides within a vehicle where the first input is captured, and wherein the first operation is performed on behalf of the user by a vehicle subsystem included in the vehicle.

3. The computer-implemented method of any of clauses 1-2, further comprising determining the first operation based on the first emotional state, and performing the first operation to assist the user.

4. The computer-implemented method of any of clauses 1-3, wherein determining the first emotional state of the user comprises determining a first feature of the first input, and determining a first type of emotion corresponding to the first feature.

5. The computer-implemented method of any of clauses 1-4, wherein the first input comprises an audio input, and wherein the first feature comprises a tone of voice associated with the user.

6. The computer-implemented method of any of clauses 1-5, wherein the first input comprises a video input, and wherein the first feature comprises a facial expression made by the user.

7. The computer-implemented method of any of clauses 1-6, wherein determining the first emotional state of the user comprises determining a first valence value based on the first input that indicates a location within a spectrum of emotion types, and determining a first intensity value based on the first input that indicates a location within a range of intensities corresponding to the location within the spectrum of emotion types.

8. The computer-implemented method of any of clauses 1-7, wherein the first emotional component corresponds to the first valence value and the first intensity value.

9. The computer-implemented method of any of clauses 1-8, wherein the first emotional component corresponds to at least one of a second valence value or a second intensity value.

10. The computer-implemented method of any of clauses 1-9, further comprising generating the first emotional component based on the first emotional state and a response mapping that translates emotional states to emotional components.

11. Some embodiments include a non-transitory computer-readable medium storing program instructions that, when executed by a processor, cause the processor to interact with a user while assisting the user by performing the steps of capturing a first input that indicates one or more behaviors associated with the user, determining a first emotional state of the user based on the first input, generating a first vocalization that incorporates a first emotional component based on the first emotional state, wherein the first vocalization relates to a first operation that is being performed to assist the user, and outputting the first vocalization to the user.

12. The non-transitory computer-readable medium of clause 11, wherein the user resides within a vehicle where the first input is captured, and wherein the first operation is performed on behalf of the user by a vehicle subsystem included in the vehicle.

13. The non-transitory computer-readable medium of any of clauses 11-12, further comprising the steps of determining the first operation based on the first emotional state, and performing the first operation to assist the user.

14. The non-transitory computer-readable medium of any of clauses 11-13, wherein the step of determining the first emotional state of the user comprises determining a first feature of the first input, and determining a first type of emotion corresponding to the first feature, wherein the first feature comprises a tone of voice associated with the user or a facial expression made by the user.

15. The non-transitory computer-readable medium of any of clauses 11-14, wherein the step of determining the first emotional state of the user comprises determining a first valence value based on the first input that indicates a location within a spectrum of emotion types, and determining a first intensity value based on the first input that indicates a location within a range of intensities corresponding to the location within the spectrum of emotion types.

16. The non-transitory computer-readable medium of any of clauses 11-15, further comprising the step of generating the first emotional component based on the first emotional state and a response mapping that translates emotional states to emotional components.

17. The non-transitory computer-readable medium of any of clauses 11-16, further comprising capturing a second input that indicates at least one behavior the user performs in response to the output, and modifying the response mapping based on the second input and a first objective function that is evaluated to determine how closely the at least one behavior corresponds to a target behavior.

18. The non-transitory computer-readable medium of any of clauses 11-17, wherein the step of generating the first vocalization comprises combining the first emotional component with a first semantic component.

19. The non-transitory computer-readable medium of any of clauses 11-18, further comprising generating a transcription of the first input that indicates one or more semantic components included in the first input, and generating the first semantic component based on the one or more semantic components.

20. Some embodiments include a system, comprising a memory storing a software application, and a processor that, when executing the software application, is configured to perform the steps of capturing a first input that indicates one or more behaviors associated with a user, determining a first emotional state of the user based on the first input, generating a first vocalization that incorporates a first emotional component based on the first emotional state, wherein the first vocalization relates to a first operation that is being performed to assist the user, and outputting the first vocalization to the user.

Any and all combinations of any of the claim elements recited in any of the claims and/or any elements described in this application, in any fashion, fall within the contemplated scope of the present embodiments and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "module," a "system," or a "computer." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

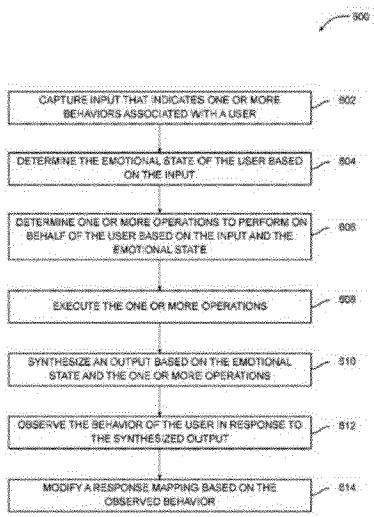

What is claimed is:

1. A computer-implemented method for causing a virtual personal assistant to interact with a user while assisting the user, the method comprising:
   capturing, by an input device of the virtual personal assistant, a first input that indicates one or more behaviors associated with the user;
   determining, by a processor of the virtual personal assistant, a first emotional state of the user based on the first input;
   selecting, by the processor using a machine learning model stored in a memory of the virtual personal assistant, a first emotional component for changing the first emotional state of the user to a first target emotional state of the user, wherein the machine learning model maps the first target emotional state of the user to the first emotional component for changing the first emotional state of the user to the first target emotional state of the user, and the machine learning model maps a second target emotional state of the user to a second emotional component for changing a second emotional state of the user to the second target emotional state of the user, wherein the first target emotional state of the user is different from the second target emotional state of the user, wherein the first emotional component comprises at least one of a pitch of speech, a laugh, a cough, a whistle, one or more non-speech alert sounds, a stress frequency of speech, a contour slope of speech, a final lowering of speech, a breathiness quality of speech, a laryngealization of speech, a pause discontinuity of speech, or a pitch continuity of speech;

generating, by the processor, a first vocalization that incorporates the first emotional component, wherein the first vocalization relates to a first operation that is being performed by the virtual personal assistant to assist the user;

outputting, by an audio output device of the virtual personal assistant, the first vocalization to the user;

capturing, by the input device of the virtual personal assistant, a second input that indicates at least one behavior the user performs in response to the outputting of the first vocalization;

determining, by the processor, an updated emotional state of the user based on the second input; and modifying, by the processor, the machine learning model based on the updated emotional state of the user and the first target emotional state of the user.

2. The computer-implemented method of claim 1, wherein the user resides within a vehicle where the first input is captured, and wherein the first operation is performed on behalf of the user by a vehicle subsystem included in the vehicle.

3. The computer-implemented method of claim 1, further comprising the steps of:
determining the first operation based on the first emotional state; and
performing the first operation to assist the user.

4. The computer-implemented method of claim 1, wherein the step of determining the first emotional state of the user comprises the steps of:
determining a first feature of the first input; and
determining a first type of emotion corresponding to the first feature.

5. The computer-implemented method of claim 4, wherein the first input comprises an audio input, and wherein the first feature comprises a tone of voice associated with the user.

6. The computer-implemented method of claim 4, wherein the first input comprises a video input, and wherein the first feature comprises a facial expression made by the user.

7. The computer-implemented method of claim 1, wherein the step of determining the first emotional state of the user comprises the steps of:
determining a first valence value based on the first input that indicates a location within a spectrum of emotion types; and
determining a first intensity value based on the first input that indicates a location within a range of intensities corresponding to the location within the spectrum of emotion types.

8. The computer-implemented method of claim 7, wherein the first emotional component corresponds to the first valence value and the first intensity value.

9. The computer-implemented method of claim 7, wherein the first emotional component corresponds to at least one of a second valence value or a second intensity value.

10. A non-transitory computer-readable medium storing program instructions that, when executed by a processor of a virtual personal assistant, cause the processor to interact with a user while assisting the user by performing the steps of:
capturing, using an input device of the virtual personal assistant, a first input that indicates one or more behaviors associated with the user;
determining a first emotional state of the user based on the first input;
selecting, using a machine learning model stored in a memory of the virtual personal assistant, a first emotional component for changing the first emotional state of the user to a first target emotional state of the user, wherein the machine learning model maps the first target emotional state of the user to the first emotional component for changing the first emotional state of the user to the first target emotional state of the user, and the machine learning model maps a second target emotional state of the user to a second emotional component for changing a second emotional state of the user to the second target emotional state of the user, wherein the first target emotional state of the user is different from the second target emotional state of the user, wherein the first emotional component comprises at least one of a pitch of speech, a laugh, a cough, a whistle, one or more non-speech alert sounds, a stress frequency of speech, a contour slope of speech, a final lowering of speech, a breathiness quality of speech, a laryngealization of speech, a pause discontinuity of speech, or a pitch continuity of speech;
generating a first vocalization that incorporates the first emotional component, wherein the first vocalization relates to a first operation that is being performed by the virtual personal assistant to assist the user;
outputting, using an audio output device of the virtual personal assistant, the first vocalization to the user;
capturing, using the input device of the virtual personal assistant, a second input that indicates at least one behavior the user performs in response to the outputting of the first vocalization;
determining an updated emotional state of the user based on the second input; and
modifying the machine learning model based on the updated emotional state of the user and the first target emotional state of the user.

11. The non-transitory computer-readable medium of claim 10, wherein the user resides within a vehicle where the first input is captured, and wherein the first operation is performed on behalf of the user by a vehicle subsystem included in the vehicle.

12. The non-transitory computer-readable medium of claim 10, further comprising the steps of:
determining the first operation based on the first emotional state; and
performing the first operation to assist the user.

13. The non-transitory computer-readable medium of claim 10, wherein the step of determining the first emotional state of the user comprises the steps of:

determining a first feature of the first input; and determining a first type of emotion corresponding to the first feature, wherein the first feature comprises a tone of voice associated with the user or a facial expression made by the user.

14. The non-transitory computer-readable medium of claim 10, wherein the step of determining the first emotional state of the user comprises the steps of:

determining a first valence value based on the first input that indicates a location within a spectrum of emotion types; and determining a first intensity value based on the first input that indicates a location within a range of intensities corresponding to the location within the spectrum of emotion types.

15. The non-transitory computer-readable medium of claim 10, wherein modifying the machine learning model further comprises modifying the machine learning model based on the second input and a first objective function that is evaluated to determine how closely the at least one behavior corresponds to a target behavior.

16. The non-transitory computer-readable medium of claim 10, wherein the step of generating the first vocalization comprises the step of combining the first emotional component with a first semantic component.

17. The non-transitory computer-readable medium of claim 16, further comprising the steps of:

generating a transcription of the first input that indicates one or more semantic components included in the first input; and generating the first semantic component based on the one or more semantic components.

18. A system of a virtual personal assistant, comprising:
a memory storing a software application; and
a processor that, when executing the software application, is configured to perform the steps of:

capturing, from an input device of the virtual personal assistant, a first input that indicates one or more behaviors associated with a user, determining a first emotional state of the user based on the first input, selecting, using a machine learning model stored in a memory of the virtual personal assistant, a first emotional component for changing the first emotional state of the user to a first target emotional state of the user, wherein the machine learning model maps the first target emotional state of the user to the first emotional component for changing the first emotional state of the user to the first target emotional state of the user, and the machine learning model maps a second target emotional state of the user to a second emotional component for changing a second emotional state of the user to the second target emotional state of the user, wherein the first target emotional state of the user is different from the second target emotional state of the user, wherein the first emotional component comprises at least one of a pitch of speech, a laugh, a cough, a whistle, one or more non-speech alert sounds, a stress frequency of speech, a contour slope of speech, a final lowering of speech, a breathiness quality of speech, a laryngealization of speech, a pause discontinuity of speech, or a pitch continuity of speech, generating a first vocalization that incorporates the first emotional component, wherein the first vocalization relates to a first operation that is being performed by the virtual personal assistant to assist the user, outputting, using an audio output device of the virtual personal assistant, the first vocalization to the user, capturing, using the input device of the virtual personal assistant, a second input that indicates at least one behavior the user performs in response to the outputting of the first vocalization, determining an updated emotional state of the user based on the second input, and modifying the machine learning model based on the updated emotional state of the user and the first target emotional state of the user.

* * * * *

UNITED STATES PATENT AND TRADEMARK OFFICE
CERTIFICATE OF CORRECTION

PATENT NO. : 11,735,206 B2
APPLICATION NO. : 16/833203
DATED : August 22, 2023
INVENTOR(S) : Joseph Verbeke, Sven Kratz and Stefan Marti It is certified that error appears in the above-identified patent and that said Letters Patent is hereby corrected as shown below:

On the Title Page

Please replace the title page with the attached title page showing the corrected number of claims.

In the Claims

Please delete "1. A computer-implemented method for causing a virtual personal assistant to interact with a user while assisting the user, the method comprising: capturing, by an input device of the virtual personal assistant, a first input that indicates one or more behaviors associated with the user; determining, by a processor of the virtual personal assistant, a first emotional state of the user based on the first input; selecting, by the processor using a machine learning model stored in a memory of the virtual personal assistant, a first emotional component for changing the first emotional state of the user to a first target emotional state of the user, wherein the machine learning model maps the first target emotional state of the user to the first emotional component for changing the first emotional state of the user to the first target emotional state of the user, and the machine learning model maps a second target emotional state of the user to a second emotional component for changing a second emotional state of the user to the second target emotional state of the user, wherein the first target emotional state of the user is different from the second target emotional state of the user, wherein the first emotional component comprises at least one of a pitch of speech, a laugh, a cough, a whistle, one or more non-speech alert sounds, a stress frequency of speech, a contour slope of speech, a final lowering of speech, a breathiness quality of speech, a laryngealization of speech, a pause discontinuity of speech, or a pitch continuity of speech; generating, by the processor, a first vocalization that incorporates the first emotional component, wherein the first vocalization relates to a first operation that is being performed by the virtual personal assistant to assist the user; outputting, by an audio output device of the virtual personal assistant, the first vocalization to the user; capturing, by the input device of the virtual personal assistant, a second input that indicates at least one behavior the user performs in response to the outputting of the first vocalization; determining, by the processor, an updated emotional state of the user based on the second input; and modifying, by the processor, the machine learning model based on the updated emotional state of the user and the first target emotional state of the user.

Signed and Sealed this
Tenth Day of September, 2024

*Katherine Kelly Vidal*
Katherine Kelly Vidal
*Director of the United States Patent and Trademark Office*

2. The computer-implemented method of claim 1, wherein the user resides within a vehicle where the first input is captured, and wherein the first operation is performed on behalf of the user by a vehicle subsystem included in the vehicle.

3. The computer-implemented method of claim 1, further comprising the steps of: determining the first operation based on the first emotional state; and performing the first operation to assist the user.

4. The computer-implemented method of claim 1, wherein the step of determining the first emotional state of the user comprises the steps of: determining a first feature of the first input; and determining a first type of emotion corresponding to the first feature.

5. The computer-implemented method of claim 4, wherein the first input comprises an audio input, and wherein the first feature comprises a tone of voice associated with the user.

6. The computer-implemented method of claim 4, wherein the first input comprises a video input, and wherein the first feature comprises a facial expression made by the user.

7. The computer-implemented method of claim 1, wherein the step of determining the first emotional state of the user comprises the steps of: determining a first valence value based on the first input that indicates a location within a spectrum of emotion types; and determining a first intensity value based on the first input that indicates a location within a range of intensities corresponding to the location within the spectrum of emotion types.

8. The computer-implemented method of claim 7, wherein the first emotional component corresponds to the first valence value and the first intensity value.

9. The computer-implemented method of claim 7, wherein the first emotional component corresponds to at least one of a second valence value or a second intensity value.

10. A non-transitory computer-readable medium storing program instructions that, when executed by a processor of a virtual personal assistant, cause the processor to interact with a user while assisting the user by performing the steps of: capturing, using an input device of the virtual personal assistant, a first input that indicates one or more behaviors associated with the user; determining a first emotional state of the user based on the first input; selecting, using a machine learning model stored in a memory of the virtual personal assistant, a first emotional component for changing the first emotional state of the user to a first target emotional state of the user, wherein the machine learning model maps the first target emotional state of the user to the first emotional component for changing the first emotional state of the user to the first target emotional state of the user, and the machine learning model maps a second target emotional state of the user to a second emotional component for changing a second emotional state of the user to the second target emotional state of the user, wherein the first target emotional state of the user is different from the second target emotional state of the user,
wherein the first emotional component comprises at least one of a pitch of speech, a laugh, a cough, a whistle, one or more non-speech alert sounds, a stress frequency of speech, a contour slope of speech, a final lowering of speech, a breathiness quality of speech, a laryngealization of speech, a pause discontinuity of speech, or a pitch continuity of speech; generating a first vocalization that incorporates the first emotional component, wherein the first vocalization relates to a first operation that is being performed by the virtual personal assistant to assist the user; outputting, using an audio output device of the virtual personal assistant, the first vocalization to the user; capturing, using the input device of the virtual personal assistant, a second input that indicates at least one behavior the user performs in response to the outputting of the first vocalization; determining an updated emotional state of the user based on the second input; and modifying the machine learning model based on the updated emotional state of the user and the first target emotional state of the user.

11. The non-transitory computer-readable medium of claim 10, wherein the user resides within a vehicle where the first input is captured, and wherein the first operation is performed on behalf of the user by a vehicle subsystem included in the vehicle.

12. The non-transitory computer-readable medium of claim 10, further comprising the steps of: determining the first operation based on the first emotional state; and performing the first operation to assist the user.

13. The non-transitory computer-readable medium of claim 10, wherein the step of determining the first emotional state of the user comprises the steps of: determining a first feature of the first input; and determining a first type of emotion corresponding to the first feature, wherein the first feature comprises a tone of voice associated with the user or a facial expression made by the user.

14. The non-transitory computer-readable medium of claim 10, wherein the step of determining the first emotional state of the user comprises the steps of: determining a first valence value based on the first input that indicates a location within a spectrum of emotion types; and determining a first intensity value based on the first input that indicates a location within a range of intensities corresponding to the location within the spectrum of emotion types.

15. The non-transitory computer-readable medium of claim 10, wherein modifying the machine learning model further comprises modifying the machine learning model based on the second input and a first objective function that is evaluated to determine how closely the at least one behavior corresponds to a target behavior.

16. The non-transitory computer-readable medium of claim 10, wherein the step of generating the first vocalization comprises the step of combining the first emotional component with a first semantic component.

17. The non-transitory computer-readable medium of claim 16, further comprising the steps of: generating a transcription of the first input that indicates one or more semantic components included in the first input; and generating the first semantic component based on the one or more semantic components.

18. A system of a virtual personal assistant, comprising: a memory storing a software application; and a processor that, when executing the software application, is configured to perform the steps of: capturing, from an input device of the virtual personal assistant, a first input that indicates one or more behaviors associated with a user, determining a first emotional state of the user based on the first input, selecting, using a machine learning model stored in a memory of the virtual personal assistant, a first emotional component for changing the first emotional state of the user to a first target emotional state of the user, wherein the machine learning model maps the first target emotional state of the user to the first emotional component for changing the first emotional state of the user to the first target emotional state of the user, and the machine learning model maps a second target emotional state of the user to a second emotional component for changing a second emotional state of the user to the second target emotional state of the user, wherein the first target emotional state of the user is different from the second target emotional state of the user, wherein the first emotional component comprises at least one of a pitch of speech, a laugh, a cough, a whistle, one or more non-speech alert sounds, a stress frequency of speech, a contour slope of speech, a final lowering of speech, a breathiness quality of speech, a laryngealization of speech, a pause discontinuity of speech, or a pitch continuity of speech, generating a first vocalization that incorporates the first emotional component, wherein the first vocalization relates to a first operation that is being performed by the virtual personal assistant to assist the user, outputting, using an audio output device of the virtual personal assistant, the first vocalization to the user, capturing, using the input device of the virtual personal assistant, a second input that indicates at least one behavior the user performs in response to the outputting of the first vocalization, determining an updated emotional state of the user based on the second input, and modifying the machine learning model based on the updated emotional state of the user and the first target emotional state of the user."

And insert --1. A computer-implemented method for causing a virtual personal assistant to interact with a user while assisting the user, the method comprising:
capturing, by an input device of the virtual personal assistant, a first input that indicates one or more behaviors associated with the user; determining, by a processor of the virtual personal assistant, that the first input includes a command to operate a subsystem of a system associated with the user; determining, by the processor, a set of eligible operations that the virtual personal assistant can cause the subsystem to perform to assist the user based on the command; determining, by the processor, a first emotional state of the user based on the first input; selecting, by the processor using a machine learning model stored in a memory of the virtual personal assistant, a subset of eligible operations included in the set of eligible operations based on the first emotional state; causing the subsystem to perform the subset of eligible operations;
selecting, by the processor using the machine learning model, a first emotional component for changing the first emotional state of the user to a first target emotional state of the user, wherein the machine learning model maps the first target emotional state of the user to the first emotional component for changing the first emotional state of the user to the first target emotional state of the user, and the machine learning model maps a second target emotional state of the user to a second emotional component for changing a second emotional state of the user to the second target emotional state of the user, wherein the first target emotional state of the user is different from the second target emotional state of the user; generating, by the processor, a first vocalization that incorporates the first emotional component, wherein the first vocalization relates to the subset of eligible operations; outputting, by an audio output device of the virtual personal assistant, the first vocalization to the user; capturing, by the input device of the virtual personal assistant, a second input that indicates at least one behavior the user performs following the subsystem performing the subset of eligible operations and the outputting of the first vocalization; determining, by the processor, an updated emotional state of the user based on the second input; and modifying, by the processor, the machine learning model based on the updated emotional state of the user and the first target emotional state of the user.
2. The computer-implemented method of claim 1, wherein the user resides within a vehicle where the first input is captured, and wherein the subset of eligible operations is performed on behalf of the user by a vehicle subsystem included in the vehicle.
3. The computer-implemented method of claim 1, wherein the step of determining the first emotional state of the user comprises the steps of: determining a first feature of the first input; and determining a first type of emotion corresponding to the first feature.
4. The computer-implemented method of claim 3, wherein the first input comprises an audio input, and wherein the first feature comprises a tone of voice associated with the user.
5. The computer-implemented method of claim 3, wherein the first input comprises a video input, and wherein the first feature comprises a facial expression made by the user.
6. The computer-implemented method of claim 1, wherein the step of determining the first emotional state of the user comprises the steps of: determining a first valence value based on the first input that indicates a location within a spectrum of emotion types; and determining a first intensity value based on the first input that indicates a location within a range of intensities corresponding to the location within the spectrum of emotion types.

7. The computer-implemented method of claim 6, wherein the first emotional component corresponds to the first valence value and the first intensity value.

8. The computer-implemented method of claim 6, wherein the first emotional component corresponds to at least one of a second valence value or a second intensity value.

9. A non-transitory computer-readable medium storing program instructions that, when executed by a processor of a virtual personal assistant, cause the processor to interact with a user while assisting the user by performing the steps of: capturing, using an input device of the virtual personal assistant, a first input that indicates one or more behaviors associated with the user; determining that the first input includes a command to operate a subsystem of a system associated with the user; determining a set of eligible operations that the virtual personal assistant can cause the subsystem to perform to assist the user based on the command; determining a first emotional state of the user based on the first input; selecting, using a machine learning model stored in a memory of the virtual personal assistant, a subset of eligible operations included in the set of eligible operations based on the first emotional state; causing the subsystem to perform the subset of eligible operations; selecting, using the machine learning model, a first emotional component for changing the first emotional state of the user to a first target emotional state of the user, wherein the machine learning model maps the first target emotional state of the user to the first emotional component for changing the first emotional state of the user to the first target emotional state of the user, and the machine learning model maps a second target emotional state of the user to a second emotional component for changing a second emotional state of the user to the second target emotional state of the user, wherein the first target emotional state of the user is different from the second target emotional state of the user; generating a first vocalization that incorporates the first emotional component, wherein the first vocalization relates to the subset of eligible operations; outputting, using an audio output device of the virtual personal assistant, the first vocalization to the user; capturing, using the input device of the virtual personal assistant, a second input that indicates at least one behavior the user performs following the subsystem performing the subset of eligible operations and the outputting of the first vocalization; determining an updated emotional state of the user based on the second input; and modifying the machine learning model based on the updated emotional state of the user and the target emotional state of the user.

10. The non-transitory computer-readable medium of claim 9, wherein the user resides within a vehicle where the first input is captured, and wherein the subset of eligible operations is performed on behalf of the user by a vehicle subsystem included in the vehicle.

11. The non-transitory computer-readable medium of claim 9, wherein the step of determining the first emotional state of the user comprises the steps of: determining a first feature of the first input; and determining a first type of emotion corresponding to the first feature, wherein the first feature comprises a tone of voice associated with the user or a facial expression made by the user.

12. The non-transitory computer-readable medium of claim 9, wherein the step of determining the first emotional state of the user comprises the steps of: determining a first valence value based on the first input that indicates a location within a spectrum of emotion types; and determining a first intensity value based on the first input that indicates a location within a range of intensities corresponding to the location within the spectrum of emotion types.

13. The non-transitory computer-readable medium of claim 9, wherein modifying the machine learning model further comprises modifying the machine learning model based on the second input and a first objective function that is evaluated to determine how closely the at least one behavior corresponds to a target behavior.

14. The non-transitory computer-readable medium of claim 9, wherein the step of generating the first vocalization comprises the step of combining the first emotional component with a first semantic component.

16. The non-transitory computer-readable medium of claim 14, further comprising the steps of: generating a transcription of the first input that indicates one or more semantic components included in the first input; and generating the first semantic component based on the one or more semantic components.

16. A system of a virtual personal assistant, comprising: a memory storing a software application; and a processor that, when executing the software application, is configured to perform the steps of: capturing, from an input device of the virtual personal assistant, a first input that indicates one or more behaviors associated with a user, determining that the first input includes a command to operate a subsystem of a system associated with the user, determining a set of eligible operations that the virtual personal assistant can cause the subsystem to perform to assist the user based on the command, determining a first emotional state of the user based on the first input, selecting, using a machine learning model stored in a memory of the virtual personal assistant, a subset of eligible operations included in the set of eligible operations based on the first emotional state, causing the subsystem to perform the subset of eligible operations, selecting, using the machine learning model, a first emotional component for changing the first emotional state of the user to a first target emotional state of the user, wherein the machine learning model maps the first target emotional state of the user to the first emotional component for changing the first emotional state of the user to the first target emotional state of the user, and the machine learning model maps a second target emotional state of the user to a second emotional component for changing a second emotional state of the user to the second target emotional state of the user, wherein the first target emotional state of the user is different from the second target emotional state of the user, generating a first vocalization that incorporates the first emotional component, wherein the first vocalization relates to the subset of eligible operations, outputting, using an audio output device of the virtual personal assistant, the first vocalization to the user, capturing, using the input device of the virtual personal assistant, a second input that indicates at least one behavior the user performs following the subsystem performing the subset of eligible operations and the outputting of the first vocalization, determining an updated emotional state of the user based on the second input, and modifying the machine learning model based on the updated emotional state of the user and the first target emotional state of the user.--.

(12) United States Patent
Verbeke et al.

(10) Patent No.: US 11,735,206 B2
(45) Date of Patent: Aug. 22, 2023

(54) EMOTIONALLY RESPONSIVE VIRTUAL PERSONAL ASSISTANT

(71) Applicant: HARMAN INTERNATIONAL INDUSTRIES, INCORPORATED, Stamford, CT (US)

(72) Inventors: Joseph Verbeke, San Francisco, CA (US); Sven Kratz, Saratoga, CA (US); Stefan Marti, Oakland, CA (US)

(73) Assignee: Harman International Industries, Incorporated, Stamford, CT (US)

( * ) Notice: Subject to any disclaimer, the term of this patent is extended or adjusted under 35 U.S.C. 154(b) by 244 days.

(21) Appl. No.: 16/833,203

(22) Filed: Mar. 27, 2020

(65) Prior Publication Data
US 2021/0304787 A1  Sep. 30, 2021

(51) Int. Cl.
G10L 25/63 (2013.01)
G06V 40/16 (2022.01)
B60W 40/08 (2012.01)

(52) U.S. Cl.
CPC .......... *G10L 25/63* (2013.01); *G06V 40/176* (2022.01); *B60W 2040/089* (2013.01)

(58) Field of Classification Search
CPC ....... G10L 25/63; G10L 13/033; G10L 15/22; B60W 40/08; B60W 2040/089; B60W 50/08; B60W 2050/0002; B60W 2050/0057; G06V 40/176; G06V 20/597; G06V 40/174; G06V 40/20; A61B 5/18; A61B 5/6893; A61B 5/165; G06F 3/011; G06F 3/167; G06F 40/216; G06F 40/35; G06F 2203/011; G06F 2203/0381; G06F 40/30; G06F 40/56
See application file for complete search history.

(56) References Cited

U.S. PATENT DOCUMENTS 9,786,299 B2 * 10/2017 Un .................. G10L 13/08
10,137,902 B2 * 11/2018 Juneja ............. B60W 40/09
(Continued)

FOREIGN PATENT DOCUMENTS

WO  2016/089929 A1  6/2016

OTHER PUBLICATIONS

Seo et al., "Automatic Emotion-Based Music Classification for Supporting Intelligent IoT Applications", Electronics, doi:10.3390/electronics8020164, vol. 8, Feb. 2019, pp. 1-20.

*Primary Examiner* — Fariba Sirjani
(74) *Attorney, Agent, or Firm* — I Artegis Law Group, LLP

(57) ABSTRACT

A virtual private assistant (VPA) is configured to analyze various types of input that indicate one or more behaviors associated with a user and to determine the emotional state of the user based on the input. The VPA also determines one or more operations to perform on behalf of the user based on the input and the determined emotional state. The VPA then executes the one or more operations and synthesizes an output based on the emotional state of the user and the one or more operations. The synthesized output includes one or more semantic components and one or more emotional components derived from the emotional state of the user. The VPA observes the behavior of the user in response to the synthesized output and then implements various modifications, based on the observed behavior, to improve the effectiveness of future interactions with the user.

16 Claims, 12 Drawing Sheets